(12) United States Patent
Hillis et al.

(10) Patent No.: US 8,092,549 B2
(45) Date of Patent: Jan. 10, 2012

(54) CILIATED STENT-LIKE-SYSTEM

(75) Inventors: W. Daniel Hillis, Encino, CA (US); Muriel Y. Ishikawa, Livermore, CA (US); Clarence T. Tegreene, Bellevue, WA (US); Richa Wilson, San Francisco, CA (US); Victoria Y. H. Wood, Livermore, CA (US); Lowell L. Wood, Jr., Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 210 days.

(21) Appl. No.: 10/949,186

(22) Filed: Sep. 24, 2004

(65) Prior Publication Data
US 2006/0069425 A1    Mar. 30, 2006

(51) Int. Cl.
*A61F 2/04* (2006.01)
(52) U.S. Cl. .................................... 623/23.64
(58) Field of Classification Search ............... 623/23.7, 623/1.15, 1.1–1.5, 23.65, 23.64; 604/8–9; 600/37, 114, 109; 606/191, 192, 151, 157
See application file for complete search history.

(56) References Cited

U.S. PATENT DOCUMENTS

| | | |
|---|---|---|
| 3,391,697 A | 7/1968 | Greatbatch |
| 3,821,469 A | 6/1974 | Whetstone et al. |
| 3,837,339 A | 9/1974 | Aisenberg et al. |
| 3,941,127 A | 3/1976 | Froning |
| 3,983,474 A | 9/1976 | Kuipers |
| 4,054,881 A | 10/1977 | Raab |
| 4,119,900 A | 10/1978 | Kremnitz |
| 4,202,349 A | 5/1980 | Jones |
| 4,262,306 A | 4/1981 | Renner |
| 4,314,251 A | 2/1982 | Raab |
| 4,317,078 A | 2/1982 | Weed et al. |
| 4,339,953 A | 7/1982 | Iwasaki |
| 4,367,741 A | 1/1983 | Michaels |
| 4,396,885 A | 8/1983 | Constant |
| 4,403,321 A | 9/1983 | Krüger |
| 4,418,422 A | 11/1983 | Richter et al. |
| 4,431,005 A | 2/1984 | McCormick |
| 4,583,190 A | 4/1986 | Salb |
| 4,585,652 A | 4/1986 | Miller et al. |
| 4,628,928 A | 12/1986 | Lowell |
| 4,638,798 A | 1/1987 | Shelden et al. |
| 4,642,786 A | 2/1987 | Hansen |
| 4,651,732 A | 3/1987 | Frederick |
| 4,658,214 A | 4/1987 | Petersen |
| 4,714,460 A | 12/1987 | Calderon |
| 4,717,381 A | 1/1988 | Papantonakos |
| 4,733,661 A | 3/1988 | Palestrant |
| 4,763,667 A | 8/1988 | Manzo |
| 4,769,006 A | 9/1988 | Papantonakos |
| 4,771,772 A | 9/1988 | DeWitt |

(Continued)

FOREIGN PATENT DOCUMENTS

CN   99810271.7   10/2001

(Continued)

OTHER PUBLICATIONS

U.S. Appl. No. 11/651,946, Ferren et al.

(Continued)

*Primary Examiner* — Alvin J. Stewart

(57) ABSTRACT

A ciliated stent-like system and method of operating the same.

74 Claims, 7 Drawing Sheets

U.S. PATENT DOCUMENTS

| | | |
|---|---|---|
| 4,800,898 A | 1/1989 | Hess et al. |
| 4,805,615 A | 2/1989 | Carol |
| 4,817,601 A | 4/1989 | Roth et al. |
| 4,871,351 A | 10/1989 | Feingold |
| 4,889,526 A | 12/1989 | Rauscher et al. |
| 4,905,689 A | 3/1990 | Stack et al. |
| 4,943,296 A | 7/1990 | Funakubo et al. |
| 4,944,659 A | 7/1990 | Labbe et al. |
| 4,962,453 A | 10/1990 | Pong et al. |
| 4,994,071 A | 2/1991 | MacGregor |
| 5,019,372 A | 5/1991 | Folkman et al. |
| 5,031,109 A | 7/1991 | Gloton |
| 5,051,906 A | 9/1991 | Evans, Jr. et al. |
| 5,078,140 A | 1/1992 | Kwoh |
| 5,086,401 A | 2/1992 | Glassman et al. |
| 5,153,827 A | 10/1992 | Coutre et al. |
| 5,165,064 A | 11/1992 | Mattaboni |
| 5,176,638 A | 1/1993 | Michael |
| 5,188,111 A | 2/1993 | Yates et al. |
| 5,204,814 A | 4/1993 | Noonan et al. |
| 5,234,457 A | 8/1993 | Andersen |
| 5,269,303 A | 12/1993 | Wernicke et al. |
| 5,279,607 A | 1/1994 | Schentag et al. |
| 5,310,404 A | 5/1994 | Gyory et al. |
| 5,313,835 A | 5/1994 | Dunn |
| 5,314,451 A | 5/1994 | Mulier |
| 5,321,614 A | 6/1994 | Ashworth |
| 5,335,657 A | 8/1994 | Terry, Jr. et al. |
| 5,337,732 A | 8/1994 | Grundfest et al. |
| 5,338,625 A | 8/1994 | Bates et al. |
| 5,339,051 A | 8/1994 | Koehler et al. |
| 5,353,807 A | 10/1994 | DeMarco |
| 5,374,285 A | 12/1994 | Vaiani et al. |
| 5,381,786 A | 1/1995 | Spears |
| 5,386,741 A | 2/1995 | Rennex |
| 5,395,390 A | 3/1995 | Simon et al. |
| 5,398,670 A | 3/1995 | Ortiz et al. |
| 5,403,311 A | 4/1995 | Abele et al. |
| 5,411,551 A | 5/1995 | Winston et al. |
| 5,437,660 A | 8/1995 | Johnson et al. |
| 5,476,450 A | 12/1995 | Ruggio |
| 5,497,147 A | 3/1996 | Arms et al. |
| 5,502,638 A | 3/1996 | Takenaka |
| 5,507,287 A | 4/1996 | Palcic et al. |
| 5,522,394 A | 6/1996 | Zurbrugg |
| 5,551,953 A | 9/1996 | Lattin et al. |
| 5,554,914 A | 9/1996 | Miyazawa |
| 5,569,968 A | 10/1996 | Lal et al. |
| 5,574,347 A | 11/1996 | Neubauer |
| 5,589,932 A | 12/1996 | Garcia-Rubio et al. |
| 5,593,434 A | 1/1997 | Williams |
| 5,599,324 A | 2/1997 | McAlister et al. |
| 5,610,488 A | 3/1997 | Miyazawa |
| 5,624,398 A | 4/1997 | Smith et al. |
| 5,632,754 A | 5/1997 | Farley et al. |
| 5,643,296 A | 7/1997 | Hundertmark et al. |
| 5,662,587 A | 9/1997 | Grundfest et al. |
| 5,669,874 A | 9/1997 | Feiring |
| 5,670,329 A | 9/1997 | Oberhardt |
| 5,674,276 A * | 10/1997 | Andersen et al. ............... 623/1.5 |
| 5,688,269 A | 11/1997 | Newton et al. |
| 5,695,457 A | 12/1997 | St. Goar et al. |
| 5,697,967 A | 12/1997 | Dinh et al. |
| 5,702,432 A | 12/1997 | Chen et al. |
| 5,705,293 A | 1/1998 | Hobson |
| 5,728,089 A | 3/1998 | Lal et al. |
| 5,737,279 A | 4/1998 | Carter |
| 5,758,298 A | 5/1998 | Guldner |
| 5,782,798 A | 7/1998 | Rise |
| 5,804,563 A | 9/1998 | Still et al. |
| 5,807,395 A | 9/1998 | Mulier et al. |
| 5,819,736 A | 10/1998 | Avny et al. |
| 5,827,190 A | 10/1998 | Palcic et al. |
| 5,830,179 A | 11/1998 | Mikus et al. |
| 5,830,207 A | 11/1998 | Leeb et al. |
| 5,831,012 A | 11/1998 | Nilsson et al. |
| 5,833,603 A | 11/1998 | Kovacs et al. |
| 5,843,139 A | 12/1998 | Goedeke et al. |
| 5,855,801 A | 1/1999 | Lin et al. |
| 5,873,835 A | 2/1999 | Hastings et al. |
| 5,908,027 A | 6/1999 | Butterfield et al. |
| 5,921,982 A | 7/1999 | Lesh et al. |
| 5,947,119 A | 9/1999 | Reznick |
| 5,954,675 A | 9/1999 | Dellagatta |
| 5,964,773 A | 10/1999 | Greenstein |
| 6,004,269 A | 12/1999 | Crowley et al. |
| 6,016,449 A | 1/2000 | Fischell et al. |
| 6,019,729 A | 2/2000 | Itoigawa et al. |
| 6,022,316 A | 2/2000 | Eppstein et al. |
| 6,053,873 A | 4/2000 | Govari et al. |
| 6,086,528 A | 7/2000 | Adair |
| 6,108,597 A | 8/2000 | Kirchner et al. |
| 6,111,520 A | 8/2000 | Allen et al. |
| 6,128,538 A | 10/2000 | Fischell et al. |
| 6,134,474 A | 10/2000 | Fischell et al. |
| 6,149,603 A | 11/2000 | Parker |
| 6,159,230 A | 12/2000 | Samuels |
| 6,164,284 A | 12/2000 | Schulman et al. |
| 6,170,488 B1 | 1/2001 | Spillman, Jr. et al. |
| 6,175,757 B1 | 1/2001 | Watkins et al. |
| 6,179,789 B1 | 1/2001 | Tu et al. |
| 6,185,452 B1 | 2/2001 | Schulman et al. |
| 6,186,986 B1 | 2/2001 | Berg et al. |
| 6,187,599 B1 | 2/2001 | Asher et al. |
| 6,197,013 B1 | 3/2001 | Reed et al. |
| 6,219,577 B1 | 4/2001 | Brown, III et al. |
| 6,221,099 B1 * | 4/2001 | Andersen et al. ............ 623/1.15 |
| 6,240,312 B1 | 5/2001 | Alfano et al. |
| 6,240,316 B1 | 5/2001 | Richmond et al. |
| 6,248,345 B1 | 6/2001 | Goldenheim et al. |
| 6,249,076 B1 | 6/2001 | Madden et al. |
| 6,255,361 B1 | 7/2001 | Rajagopalan et al. |
| 6,255,793 B1 | 7/2001 | Peless et al. |
| 6,263,245 B1 | 7/2001 | Snell |
| 6,278,379 B1 | 8/2001 | Allen et al. |
| 6,289,270 B1 | 9/2001 | Baumgarten |
| 6,295,990 B1 | 10/2001 | Lewis et al. |
| 6,296,638 B1 | 10/2001 | Davison et al. |
| 6,322,532 B1 | 11/2001 | D'Sa et al. |
| 6,337,997 B1 | 1/2002 | Rise |
| 6,372,248 B1 | 4/2002 | Qin et al. |
| 6,383,162 B1 | 5/2002 | Sugarbaker |
| 6,384,741 B1 | 5/2002 | O'Leary, Sr. |
| 6,385,472 B1 | 5/2002 | Hall et al. |
| 6,398,280 B1 | 6/2002 | Parker et al. |
| 6,402,678 B1 | 6/2002 | Fischell et al. |
| 6,409,674 B1 | 6/2002 | Brockway et al. |
| 6,417,641 B2 | 7/2002 | Peless et al. |
| 6,436,120 B1 | 8/2002 | Meglin |
| 6,442,413 B1 | 8/2002 | Silver |
| 6,450,937 B1 | 9/2002 | Mercereau et al. |
| 6,453,199 B1 | 9/2002 | Kobozev |
| 6,464,687 B1 | 10/2002 | Ishikawa et al. |
| 6,475,639 B2 | 11/2002 | Shahinpoor et al. |
| 6,490,483 B2 | 12/2002 | Willis |
| 6,493,607 B1 | 12/2002 | Bourne et al. |
| 6,497,714 B1 | 12/2002 | Ishikawa et al. |
| 6,500,174 B1 | 12/2002 | Maguire et al. |
| 6,512,949 B1 | 1/2003 | Combs et al. |
| 6,512,950 B2 | 1/2003 | Li et al. |
| 6,514,237 B1 | 2/2003 | Maseda |
| 6,530,950 B1 | 3/2003 | Alvarado et al. |
| 6,547,723 B1 | 4/2003 | Ouchi |
| 6,547,825 B1 | 4/2003 | Shimizu et al. |
| 6,548,982 B1 | 4/2003 | Papanikolopoulos et al. |
| 6,554,798 B1 | 4/2003 | Mann et al. |
| 6,575,969 B1 | 6/2003 | Rittman, III et al. |
| 6,585,763 B1 | 7/2003 | Keilman et al. |
| 6,591,137 B1 | 7/2003 | Fischell et al. |
| 6,592,567 B1 | 7/2003 | Levin et al. |
| 6,597,954 B1 | 7/2003 | Pless et al. |
| 6,607,553 B1 | 8/2003 | Healy et al. |
| 6,612,982 B1 | 9/2003 | Ouchi |
| 6,616,676 B2 | 9/2003 | Bashiri et al. |
| 6,623,519 B2 | 9/2003 | Edwin et al. |
| 6,632,216 B2 | 10/2003 | Houzego et al. |
| 6,638,273 B1 | 10/2003 | Farley et al. |

| Patent | Date | Name |
|---|---|---|
| 6,648,908 B2 | 11/2003 | Dobak, III et al. |
| 6,666,860 B1 | 12/2003 | Takahashi |
| 6,669,683 B2 | 12/2003 | Santini, Jr. et al. |
| 6,673,042 B1 | 1/2004 | Samson et al. |
| 6,673,363 B2 | 1/2004 | Luo et al. |
| 6,679,893 B1 | 1/2004 | Tran |
| 6,709,388 B1 | 3/2004 | Mosse et al. |
| 6,711,423 B2 | 3/2004 | Colvin, Jr. |
| 6,712,835 B2 | 3/2004 | Mazzocchi et al. |
| 6,719,684 B2 | 4/2004 | Kim et al. |
| 6,735,474 B1 | 5/2004 | Loeb et al. |
| 6,735,475 B1 | 5/2004 | Whitehurst et al. |
| 6,743,211 B1 | 6/2004 | Prausnitz et al. |
| 6,754,536 B2 | 6/2004 | Swoyer et al. |
| 6,755,802 B2 | 6/2004 | Bell |
| 6,755,803 B2 | 6/2004 | Le et al. |
| 6,764,441 B2 | 7/2004 | Chiel et al. |
| 6,773,429 B2 | 8/2004 | Sheppard, Jr. et al. |
| 6,776,165 B2 | 8/2004 | Jin |
| 6,797,522 B1 | 9/2004 | Still et al. |
| 6,802,811 B1 | 10/2004 | Slepian |
| 6,816,632 B1 | 11/2004 | Slice |
| 6,824,508 B2 | 11/2004 | Kim et al. |
| 6,824,510 B2 | 11/2004 | Kim et al. |
| 6,824,561 B2 | 11/2004 | Soykan et al. |
| 6,834,118 B2 | 12/2004 | Kim |
| 6,849,183 B2 | 2/2005 | Gorsuch et al. |
| 6,855,115 B2 | 2/2005 | Fonseca et al. |
| 6,860,867 B2 | 3/2005 | Seward et al. |
| 6,861,001 B2 | 3/2005 | Lee et al. |
| 6,866,626 B2 | 3/2005 | Long et al. |
| 6,875,209 B2 | 4/2005 | Zvuloni et al. |
| 6,889,091 B2 | 5/2005 | Hine et al. |
| 6,890,303 B2 | 5/2005 | Fitz |
| 6,898,464 B2 | 5/2005 | Edell et al. |
| 6,911,004 B2 | 6/2005 | Kim et al. |
| 6,911,496 B2 | 6/2005 | Rhee et al. |
| 6,920,359 B2 | 7/2005 | Meadows et al. |
| 6,921,413 B2 | 7/2005 | Mahadevan-Jansen et al. |
| 6,925,357 B2 | 8/2005 | Wang et al. |
| 6,929,636 B1 | 8/2005 | Von Alten |
| 6,936,003 B2 | 8/2005 | Iddan |
| 6,939,290 B2 | 9/2005 | Iddan |
| 6,939,376 B2 | 9/2005 | Shulze et al. |
| 6,950,707 B2 | 9/2005 | Whitehurst |
| 6,953,589 B1 | 10/2005 | Trautman et al. |
| 6,958,034 B2 | 10/2005 | Iddan |
| 6,959,215 B2 | 10/2005 | Gliner et al. |
| 6,960,227 B2 | 11/2005 | Jones et al. |
| 6,963,792 B1 | 11/2005 | Green |
| 6,984,205 B2 | 1/2006 | Gazdzinski |
| 6,984,952 B2 | 1/2006 | Peless et al. |
| 6,991,617 B2 | 1/2006 | Hektner et al. |
| 7,003,352 B1 | 2/2006 | Whitehurst |
| 7,013,177 B1 | 3/2006 | Whitehurst et al. |
| 7,020,231 B1 | 3/2006 | Frey et al. |
| 7,027,134 B1 | 4/2006 | Garcia-Rubio et al. |
| 7,037,343 B2 * | 5/2006 | Imran .................. 623/23.65 |
| 7,039,453 B2 | 5/2006 | Mullick et al. |
| 7,042,184 B2 | 5/2006 | Oleynikov et al. |
| RE39,133 E | 6/2006 | Clayton et al. |
| 7,083,578 B2 | 8/2006 | Lewkowicz et al. |
| 7,101,386 B2 | 9/2006 | Dobak, III |
| 7,115,109 B2 | 10/2006 | Gerdts et al. |
| 7,118,531 B2 | 10/2006 | Krill |
| 7,125,382 B2 | 10/2006 | Zhou et al. |
| 7,131,979 B2 | 11/2006 | DiCarlo et al. |
| 7,160,258 B2 | 1/2007 | Imran et al. |
| 7,171,285 B2 | 1/2007 | Kim et al. |
| 7,181,261 B2 | 2/2007 | Silver et al. |
| 7,212,110 B1 | 5/2007 | Martin et al. |
| 7,214,182 B2 | 5/2007 | Shimizu et al. |
| 7,228,162 B2 | 6/2007 | Ward et al. |
| 7,236,821 B2 | 6/2007 | Cates et al. |
| 7,245,954 B2 | 7/2007 | Glukhovsky |
| 7,297,113 B1 | 11/2007 | Russell et al. |
| 7,341,577 B2 | 3/2008 | Gill |
| 7,365,509 B2 | 4/2008 | Park et al. |
| 7,365,614 B2 | 4/2008 | McCorquodale et al. |
| 7,383,071 B1 | 6/2008 | Russell et al. |
| 7,398,734 B1 | 7/2008 | Jean |
| 7,451,537 B2 | 11/2008 | Liu et al. |
| 7,486,967 B2 | 2/2009 | Pan et al. |
| 7,572,228 B2 | 8/2009 | Wolinsky et al. |
| 7,596,403 B2 | 9/2009 | Horn |
| 7,625,338 B2 | 12/2009 | Gilad et al. |
| 7,684,840 B2 | 3/2010 | Palti |
| 7,713,196 B2 | 5/2010 | Baker, Jr. |
| 7,736,300 B2 | 6/2010 | Ziegler et al. |
| 7,744,542 B2 | 6/2010 | Piaget et al. |
| 7,801,626 B2 | 9/2010 | Moser |
| 7,840,271 B2 | 11/2010 | Kieval et al. |
| 7,857,767 B2 | 12/2010 | Ferren et al. |
| 2001/0029348 A1 | 10/2001 | Willis |
| 2001/0051766 A1 | 12/2001 | Gazdzinski |
| 2002/0065509 A1 | 5/2002 | Lebel et al. |
| 2002/0068080 A1 | 6/2002 | Lerner |
| 2002/0090388 A1 | 7/2002 | Humes et al. |
| 2002/0103417 A1 | 8/2002 | Gazdzinski |
| 2002/0116029 A1 | 8/2002 | Miller et al. |
| 2002/0116034 A1 | 8/2002 | Miller et al. |
| 2002/0147480 A1 | 10/2002 | Mamayek |
| 2002/0156462 A1 | 10/2002 | Stultz |
| 2002/0165592 A1 | 11/2002 | Glukhovsky et al. |
| 2002/0169436 A1 | 11/2002 | Gurm et al. |
| 2002/0171385 A1 | 11/2002 | Kim et al. |
| 2002/0188323 A1 | 12/2002 | Penner et al. |
| 2002/0193679 A1 | 12/2002 | Malave et al. |
| 2002/0193874 A1 | 12/2002 | Crowley |
| 2002/0198470 A1 | 12/2002 | Imran et al. |
| 2002/0198521 A1 | 12/2002 | Maguire |
| 2002/0198604 A1 | 12/2002 | Schulman et al. |
| 2003/0024534 A1 | 2/2003 | Silvestri et al. |
| 2003/0040704 A1 | 2/2003 | Dorros et al. |
| 2003/0060723 A1 | 3/2003 | Joo et al. |
| 2003/0065250 A1 | 4/2003 | Chiel et al. |
| 2003/0065358 A1 | 4/2003 | Frecker et al. |
| 2003/0069475 A1 | 4/2003 | Banik et al. |
| 2003/0069523 A1 | 4/2003 | Williams et al. |
| 2003/0093031 A1 | 5/2003 | Long et al. |
| 2003/0151524 A1 | 8/2003 | Clark |
| 2003/0152823 A1 | 8/2003 | Heller |
| 2003/0153866 A1 | 8/2003 | Long et al. |
| 2003/0158584 A1 | 8/2003 | Cates et al. |
| 2003/0163177 A1 | 8/2003 | Eggers et al. |
| 2003/0167000 A1 | 9/2003 | Mullick et al. |
| 2003/0191430 A1 | 10/2003 | D'Andrea et al. |
| 2003/0214579 A1 | 11/2003 | Iddan |
| 2003/0214580 A1 | 11/2003 | Iddan |
| 2003/0220556 A1 | 11/2003 | Porat et al. |
| 2004/0008853 A1 | 1/2004 | Pelrine et al. |
| 2004/0018508 A1 | 1/2004 | Friedman |
| 2004/0019374 A1 | 1/2004 | Hojeibane et al. |
| 2004/0064093 A1 | 4/2004 | Hektner et al. |
| 2004/0073177 A1 | 4/2004 | Hickle |
| 2004/0073190 A1 | 4/2004 | Deem et al. |
| 2004/0092825 A1 | 5/2004 | Madar et al. |
| 2004/0097819 A1 | 5/2004 | Duarte |
| 2004/0098030 A1 | 5/2004 | Makower et al. |
| 2004/0111019 A1 | 6/2004 | Long |
| 2004/0133147 A1* | 7/2004 | Woo ............................ 604/9 |
| 2004/0138517 A1 | 7/2004 | Osorio et al. |
| 2004/0147939 A1 | 7/2004 | Rabkin et al. |
| 2004/0148034 A1 | 7/2004 | Kagan et al. |
| 2004/0152988 A1 | 8/2004 | Weirich |
| 2004/0162469 A1 | 8/2004 | Imran |
| 2004/0162501 A1 | 8/2004 | Imran |
| 2004/0176664 A1 | 9/2004 | Iddan |
| 2004/0193010 A1 | 9/2004 | Fujimori et al. |
| 2004/0199246 A1 | 10/2004 | Chu et al. |
| 2004/0225325 A1 | 11/2004 | Bonutti |
| 2004/0225326 A1 | 11/2004 | Weiner et al. |
| 2004/0260391 A1 | 12/2004 | Santini, Jr. et al. |
| 2004/0267240 A1 | 12/2004 | Gross et al. |
| 2005/0004474 A1 | 1/2005 | Iddan |
| 2005/0004553 A1 | 1/2005 | Douk |
| 2005/0021023 A1 | 1/2005 | Guglielmi et al. |
| 2005/0027236 A1 | 2/2005 | Douk |

| | | | |
|---|---|---|---|
| 2005/0043583 | A1 | 2/2005 | Killmann et al. |
| 2005/0058701 | A1 | 3/2005 | Gross et al. |
| 2005/0062562 | A1 | 3/2005 | Ries |
| 2005/0065592 | A1 | 3/2005 | Holzer |
| 2005/0069925 | A1 | 3/2005 | Ford et al. |
| 2005/0079132 | A1 | 4/2005 | Wang et al. |
| 2005/0107870 | A1 | 5/2005 | Wang et al. |
| 2005/0113460 | A1 | 5/2005 | Glick |
| 2005/0121411 | A1 | 6/2005 | Cohen |
| 2005/0126916 | A1 | 6/2005 | Lockard et al. |
| 2005/0149170 | A1 | 7/2005 | Tassel et al. |
| 2005/0151524 | A1 | 7/2005 | Sae-Ueng et al. |
| 2005/0171418 | A1 | 8/2005 | Lin |
| 2005/0171434 | A1 | 8/2005 | Madden et al. |
| 2005/0177223 | A1 | 8/2005 | Palmaz |
| 2005/0182482 | A1 | 8/2005 | Wang et al. |
| 2005/0203613 | A1 | 9/2005 | Arney et al. |
| 2005/0215911 | A1 | 9/2005 | Alfano et al. |
| 2005/0216074 | A1 | 9/2005 | Sahatjian et al. |
| 2005/0221529 | A1 | 10/2005 | Bang et al. |
| 2005/0228259 | A1 | 10/2005 | Glukhovsky et al. |
| 2005/0234393 | A1 | 10/2005 | Wood |
| 2005/0234440 | A1 | 10/2005 | Wood |
| 2005/0238689 | A1 | 10/2005 | Carpenter et al. |
| 2005/0272806 | A1 | 12/2005 | Falotico et al. |
| 2005/0272974 | A1 | 12/2005 | Iddan |
| 2005/0277839 | A1 | 12/2005 | Alderman et al. |
| 2005/0278020 | A1 | 12/2005 | Wang et al. |
| 2006/0004395 | A1 | 1/2006 | Chiel et al. |
| 2006/0009810 | A1 | 1/2006 | Mann et al. |
| 2006/0015146 | A1 | 1/2006 | Girouard et al. |
| 2006/0037617 | A1 | 2/2006 | Walke et al. |
| 2006/0042631 | A1 | 3/2006 | Martin et al. |
| 2006/0074479 | A1 | 4/2006 | Bailey et al. |
| 2006/0119304 | A1 | 6/2006 | Farritor et al. |
| 2006/0152309 | A1 | 7/2006 | Mintchev et al. |
| 2006/0167339 | A1 | 7/2006 | Gilad et al. |
| 2006/0169294 | A1 | 8/2006 | Kaler et al. |
| 2006/0235275 | A1 | 10/2006 | Rabinovitz et al. |
| 2006/0252987 | A1 | 11/2006 | Hasegawa et al. |
| 2007/0010868 | A1 | 1/2007 | Ferren et al. |
| 2007/0066929 | A1 | 3/2007 | Ferren et al. |
| 2007/0088334 | A1 | 4/2007 | Hillis et al. |
| 2007/0156211 | A1 | 7/2007 | Ferren et al. |
| 2007/0225634 | A1 | 9/2007 | Ferren et al. |
| 2008/0063703 | A1 | 3/2008 | Gross et al. |
| 2008/0066929 | A1 | 3/2008 | Costa et al. |
| 2008/0103440 | A1 | 5/2008 | Ferren et al. |
| 2008/0121054 | A1 | 5/2008 | Goldenberg et al. |
| 2008/0241847 | A1 | 10/2008 | Hoon et al. |
| 2008/0243056 | A1 | 10/2008 | Hillis et al. |
| 2008/0266106 | A1 | 10/2008 | Lim et al. |
| 2009/0062646 | A1 | 3/2009 | Creighton, IV et al. |
| 2009/0069821 | A1 | 3/2009 | Farritor et al. |
| 2009/0082652 | A1 | 3/2009 | Koh et al. |
| 2009/0182388 | A1 | 7/2009 | Von Arx et al. |

FOREIGN PATENT DOCUMENTS

| | | |
|---|---|---|
| EP | 1 245 201 A1 | 10/2002 |
| EP | 1 618 831 A2 | 1/2006 |
| EP | 2 163 206 A1 | 3/2010 |
| JP | 2001-506871 | 3/1998 |
| JP | 2002-153569 | 5/2002 |
| JP | 2005-74229 | 3/2005 |
| WO | WO 96/39999 | 12/1996 |
| WO | WO 98/09582 | 3/1998 |
| WO | WO 98/14243 | 4/1998 |
| WO | WO 99/20335 | 4/1999 |
| WO | WO 99/44665 | 9/1999 |
| WO | WO 00/69515 | 11/2000 |
| WO | WO 01/08548 A1 | 2/2001 |
| WO | WO 01/24731 A1 | 4/2001 |
| WO | WO 03/072157 A1 | 9/2003 |
| WO | WO 03/090618 A2 | 11/2003 |
| WO | WO 03/106966 A2 | 12/2003 |
| WO | WO 2004/028335 A2 | 4/2004 |
| WO | WO 2004/058041 A2 | 7/2004 |
| WO | WO 2004/086958 A1 | 10/2004 |
| WO | WO 2005/082248 A1 | 9/2005 |

OTHER PUBLICATIONS

U.S. Appl. No. 11/645,358, Ferren et al.
U.S. Appl. No. 11/645,357, Ferren et al.
U.S. Appl. No. 11/485,619, Hillis et al.
U.S. Appl. No. 11/478,368, Ferren et al.
U.S. Appl. No. 11/417,898, Hillis et al.
U.S. Appl. No. 11/403,230, Ferren et al.
UK Intellectual Property Office Examination Report Under Section 18(3), App. No. GB0821523.8; Jul. 2, 2009; pp. 1-2.
UK Intellectual Property Office Examination Report Under Section 18(3); App. No. GB0821519.6; Nov. 12, 2009; 1-4.
UK Intellectual Property Office Examination Report Under Section 18(3); App. No. GB0821526.1; Nov. 11, 2009; 1-5.
UK Intellectual Property Office Examination Report Under Section 18(3); App. No. GB0706802.6; Nov. 23, 2009; pp. 1-2.
UK Examination Report Under Section 18(3); App. No. GB0821524.6; bearing a date of May 6, 2010; pp. 1-3.
UK Intellectual Property Office Examination Report under Section 18(3); App. No. GB0821521.2; Jan. 12, 2011; pp. 1-4.
U.S. Appl. No. 12/928,455, Wood, Jr., Lowell L.
U.S. Appl. No. 12/930,916, Wood, Jr., Lowell.
UK Intellectual Property Office Examination Report Under Section 18(3); App. No. GB0821526.1; bearing a date of Jul. 15, 2010; pp. 1-2.
UK Intellectual Property Office Examination Report Under Section 18(3); App. No. GB0821524.6; Aug. 9, 2010; pp. 1-2.
UK Intellectual Property Office Examination Report Under Section 18(3); App. No. GB0821519.6; Aug. 9, 2010; pp. 1-3.
UK Intellectual Property Office Examination Report Under Section 18(3); App. No. GB0821530.3; Aug. 27, 2010; pp. 1-6.
Japanese Office Action; Japanese App. No. 2007-533572; Sep. 22, 2010; pp. 1-4; (no English translation currently available).
UK Intellectual Property Office Examination Report Under Section 18(3); App. No. GB0821519.6; Oct. 19, 2010; 1 page.
UK Intellectual Property Office Combined Search and Examination Report Under Sections 17 & 18(3); App. No. GB1016383.0 ; Nov. 1, 2010; pp. 1-4.
UK Intellectual Property Office Examination Report Under Section 18(3); App. No. GB0706802.6; bearing a date of Dec. 1, 2008; pp. 1-2.
U.S. Appl. No. 12/075,480, Hillis et al.
U.S. Appl. No. 11/891,573, Wood, Jr., Lowell L.
U.S. Appl. No. 11/891,371, Wood, Jr., Lowell L.
U.S. Appl. No. 11/891,356, Wood, Jr., Lowell L.
U.S. Appl. No. 11/891,355, Wood, Jr., Lowell L.
U.S. Appl. No. 11/891,334, Wood, Jr., Lowell L.
U.S. Appl. No. 11/891,333, Wood, Jr., Lowell L.
U.S. Appl. No. 11/726,031, Ferren et al.
U.S. Appl. No. 11/726,025, Ferren et al.
U.S. Appl. No. 11/725,982, Ferren et al.
"001_08 Comparison of Capsule Cameras: M2A (Given Imaging) vs. NORIKA3 (RF System lab)" RF System lab; bearing dates of 2001-2004; pp. 1-2; located at http://www.rfnorika.com/eng/system/sys_008.html; printed on May 4, 2006.
"A Hydrogel-based CO2 sensor"; BIOS—The lab on a chip group; bearing a date of Aug. 29, 2005; pp. 1-2; located at: http://bios.ewi.utwente.nl/research/analysissystemssenors/ahydrogelbased.doc/index.html; printed on Apr. 25, 2006; University of Twente; the Netherlands.
"Agile new plastics change shape with heat"; MIT News Office; Nov. 20, 2006; pp. 1-4; Massachusetts Institute of Technology; printed on Nov. 22, 2006; located at http://web.mit.edu/newsoffice/2006/triple-shape.html.
"Agile new plastics change shape with heat"; MIT Tech Talk; Nov. 22, 2006; p. 5 (1 page).
Ananthaswamy, Anil; "First robot moved by muscle power"; bearing a date of Feb. 27, 2004; pp. 1-3; New Scientist; located at http://www.newscientist.com/article.ns?id=dn4714; printed on Sep. 12, 2006.
Asari, Vijayan K.; Kumar, Sanjiv; Kassim, Irwan M.; "A Fully Autonomous Microrobotic Endoscopy System"; Journal of Intelligent and Robotic Systems; bearing a date of 2000; pp. 325-341; vol. 28; Kluwer Academic Publishers.

Behkam, Bahareh; SITTI, Metin; "Towards Hybrid Swimming Microrobots: Bacteria Assisted Propulsion of Polystyrene Beads"; Proceedings of the 28$^{th}$ IEEE EMBS Annual International Conference; bearing dates of Aug. 30, 2006-Sep. 3, 2006 and 2006; pp. 2421-2424; IEEE.

Berlinger, Norman T.; "Robotic Surgery—Squeezing into Tight Places"; New England Journal of Medicine; bearing dates of May 17, 2006, May 18, 2006, and 2006; pp. 2099-2101; Massachusetts Medical Society; located at www.nejm.org.

Bezrouk, A.; Hanuš, J.; Záhora, J.; "Temperature Characteristics of Nitinol Spiral Stents"; Scripta Medica (BRNO); bearing dates of Aug. 2005, Oct. 2005; pp. 219-226; vol. 78, No. 4.

Bialek, William; Rieke, Fred; De Ruyter Van Steveninck, Rob R.; Warland, David; "Reading a Neural Code"; Science; bearing a date of Jun. 28, 1991; pp. 1854-1857; vol. 252.

Bucher, Volker; Graf, Michael; Stelzle, Martin; Nisch, Wilfried; "Low-Impedance Thin-Film Polycrystalline Silicon Microelectrodes for Extracellular Stimulation and Recording"; Biosensors and Bioelectronics; bearing a date of 1999; pp. 639-649; vol. 14; Elsevier Science S.A.; located at: www.elsevier.com/locate/bios.

Butson, Christopher R.; McIntyre, Cameron C.; "Role of Electrode Design on the Volume of Tissue Activated During Deep Brain Stimulation"; Journal of Neural Engineering; bearing a date of 2006; vol. 3; pp. 1-8; IOP Publishing Ltd.

Chang, Suk Tai; Paunov, Vesselin N.; Petsev, Dimiter N.; Velev, Orlin D.; "Articles: Remotely Powered Self-Propelling Particles and Micropumps Based on Miniature Diodes"; Nature Materials; bearing a date of 2007; pp. 1-6; Nature Publishing Group; located at: www.nature.com/naturematerials.

Chen, Ting; Barton, Scott Calabrese, Binyamin, Gary; Gao, Zhiqiang; Zhang, Yongchao, Kim, Hyug-Han; Heller, Adam; "A Miniature Biofuel Cell"; Journal of the American Chemical Society; Aug. 11, 2001; pp. 8630-8631; vol. 123; 2001 American Chemical Society.

Christensen, Bill; "Musclebot: Microrobot with a Heart"; Technovelgy.com; pp. 1-2; bearing a date of Feb. 27, 2004; located at http://www.technovelgy.com/ct/Science-Fiction-News.asp?NewsNum=46; printed on Sep. 12, 2006.

Christensen, Bill; "Propulsion System for 'Fantastic Voyage' Robot"; Technovelgy.com; pp. 1-4; Technovelgy.com; located http://www.technovelgy.com/ct/Science-Fiction-News.asp?NewsNum=811; printed on Jan. 4, 2007.

Costamagna; Guido M.D.; "PillCam™ SB Capsule Endoscopy"; Given Imaging.com; bearing dates of 2001-2006; pp. 1-4; located at http://www.givenimaging.com/Cultures/en-US/Given/English/Products/CapsuleEndoscopy/; printed on May 4, 2006.

Cui, Xinyan; Hetke, Jamille F.; Wiler, James A.; Anderson, David J.; Martin, David C.; "Electrochemical Deposition and Characterization of Conducting Polymer Polypyrrole/PPS on Multichannel Neural Probes"; Sensors and Actuators A Physical; bearing a date of 2001; pp. 8-18; vol. 93; Elsevier Science B.V.; located at: www.elsevier.com/locate/sna.

Dario, P.; Carrozza, M.C.; Lencioni, L.; Magnani, B.; D'Attanasio, S.; "A Micro Robotic System for Colonoscopy"; Proceedings of the 1997 IEEE International Conference on Robotics and Automation; bearing dates of Apr. 1997 and 1997; pp. 1567-1572; IEEE.

Dillier, Norbert; Lai, Wai Kong; Almqvist, Bengt; Frohne, Carolin; Müller-Deile, Joachim; Stecker, Matthias; Von Wallenberg, Ernst; "Measurement of the Electrically Evoked Compound Action Potential Via a Neural Response Telemetry System"; Annals of Otology Rhinology and Laryngology; bearing a date of May 2002; pp. 407-414; vol. 111, No. 5; Annals Publishing Company.

Dongxiang, Chi; Guozheng, Yan; "An earthworm based miniature robot for intestinal inspection"; Proceedings of SPIE; bearing dates of Nov. 7, 2001-Nov. 9, 2001; pp. 396-400; vol. 4601; SPIE.

Donoghue, John P.; "Review: Connecting Cortex to Machines: Recent Advances in Brain Interfaces"; Nature Neuroscience Supplement; bearing a date on Nov. 2002; pp. 1085-1088; vol. 5; Nature Publishing Group; located at: http://www.nature.com/natureneuroscience.

Fang, Zi-Ping; Mortimer, J. Thomas; "Selective Activation of Small Motor Axons by Quasitrapezoidal Current Pulses"; IEEE Transactions on Biomedical Engineering; bearing a date of Feb. 1991; pp. 168-174; vol. 38, No. 2; IEEE.

Fiaccabrino, G.C.; Tang, X.-M.; Skinner, N.; De Rooij, N.F.; Koudelka-Hep, M.; "Electrochemical Characterization of Thin-Film Carbon Interdigitated Electrode Arrays"; Analytica Chimica Acta; bearing a date of 1996; pp. 155-160; vol. 326; Elsevier Science B.V.

Freitas Jr., Robert A.; "8.2.1.2 Arteriocenous Microcirculation"; "9.4.3.5 Legged Ambulation"; "9.4.3.6 Tank-Tread Rolling"; "9.4.3.7 Amoeboid Locomotion"; "9.4.3.8 Inchworm Locomotion"; "Nanomedicine vol. I: Basic Capabilities"; bearing a date of 1999; pp. 211-214, pp. 316-318; Landes Bioscience; Georgetown, Texas, USA.

Gitter, Alfred H.; Fromm, Michael; Schulzke, Jörg-Dieter; "Impedance Analysis for the Determination of Epithelial and Subepithelial Resistance in Intestinal Tissues"; Journal of Biochemical and Biophysical Methods; bearing a date of 1998; pp. 35-46; vol. 37; Elsevier Science B.V.

Goda, Yukiko; Colicos, Michael A.; "Protocol: Photoconductive Stimulation of Neurons Cultured on Silicon Wafers"; Nature Protocols; bearing a date of 2006; pp. 461-467; vol. 1, No. 1; Nature Publishing Group; located at: http://www.nature.com/natureprotocols.

Gozani, Shai N.; Miller, John P.; "Optimal Discrimination and Classification of Neuronal Action Potential Waveforms from Multiunit, Multichannel Recordings Using Software-Based Linear Filters"; IEEE Transactions on Biomedical Engineering; bearing a date of Apr. 1994; pp. 358-372; vol. 41, No. 4; IEEE.

Gray, Charles M.; Maldonado, Pedro E.; Wilson, Mathew; McNaughton, Bruce; "Tetrodes Markedly Improve the Reliability and Yield of Multiple Single-Unit Isolation from Multi-Unit Recordings in Cat Striate Cortex"; Journal of Neuroscience Methods; bearing a date of 1995; pp. 43-54; vol. 63; Elsevier Science B.V.

Hagleitner, C.; Hierlemann, A.; Lange, D.; Kummer, A.; Kerness, N.; Brand, O.; Baltes, H.; "Smart single-chip gas sensor microsystem"; Nature; Nov. 15, 2001; pp. 293-296; vol. 414; Macmillan Magazines Ltd.; www.nature.com.

Hanna, Darrin M.; Oakley, Barbara A.; Stryker, Gabrielle A.; "Using a System-on-Chip Implantable Device to Filter Circulating Infected Cells in Blood or Lymph"; IEEE Transactions on Biomedical Engineering; bearing dates of Jan. 25, 2003, Mar. 2003; pp. 6-13; vol. 2, No. 1; IEEE.

Hodgkin, A.L.; Huxley, A.F.; "A Quantitative Description of Membrane Current and its Application to Conduction and Excitation in Nerve"; Journal of Physiology; bearing a date of 1952; pp. 500-544; vol. 117.

Høeg, H.D.; Slatkin, A.B.; Burdick, J.W.; Grundfest, Dr. Warren S.; "Biomechanical Modeling of the Small Intestine as Required for the Design and Operation of a Robotic Endoscope"; Proceedings ICRA '00 IEEE International Conference on Robotics and Automation; Apr. 24, 2000-Apr. 28, 2000; pp. 1-8; vol. 2.

Hofmann, U.G.; Folkers, A.; Mösch, F.; Höhl, D.; Kindlundh, M.; Norlin, P.; "A 64(128)-Channel Multisite Neuronal Recording System"; bearing a date of 2002; pp. 1-4.

Ikeuchi, K.; Yoshinaka, K.; Hashimoto, S.; Tomita, N.; "Locomotion of Medical Micro Robot with Spiral Ribs Using Mucus"; Seventh International Symposium on Micro Machine and Human Science; bearing a date of 1996; pp. 217-222; IEEE.

Inmann, Andreas; Haugland, Morten; Haase, Jens; Biering-Sørensen, Fin; Sinkjaer, Thomas; "NeuroReport: Signals from Skin Mechanoreceptors used in Control of a Hand Grasp Neuroprosthesis"; Motor Systems; bearing a date of Sep. 17, 2001; pp. 2817-2819; vol. 12, No. 13; Lippincott Williams & Wilkins.

Janders, M.; Egert, U.; Stelze, M.; Nisch, W.; "Novel Thin Film Titanium Nitride Micro-Electrodes with Excellent Charge Transfer Capability for Cell Stimulation and Sensing Applications"; IEEE Engineering in Medicine and Biology Society; bearing a date of 1996; pp. 245-247; IEEE.

"Japanese Researchers Unveil Medical Mini Robot"; Yahoo! News; bearing a date of Mar. 8, 2007; pp. 1-2; Yahoo! Inc.; located at: http://news.yahoo.com/s/afp/20070308/h1_afp/afplifestyleshealthscience; printed on Mar. 8, 2007.

Ji, Jin; Najafi, Khalil, Wise, Kensall D.; "A Low-Noise Demultiplexing System for Active Multichannel Microelectrode Arrays"; IEEE Transactions of Biomedical Engineering; bearing a date of Jan. 1991; pp. 77-81; vol. 38, No. 1; IEEE.

Kassim, Irwan; Phee, Louis; Ng, Wan S.; Gong, Feng; Dario, Paolo; Mosse, Charles A.; "Locomotion Techniques for Robotic Colonoscopy"; IEEE Engineering in Medicine and Biology Magazine; bearing dates of May/Jun. 2006 and 2006; pp. 49-56; IEEE.

Kennedy, P.R.; Bakay, R.A.E.; Moore, M.M.; Adams, K.; Goldwaithe, J.; "Direct Control of a Computer from the Human Central Nervous System"; IEEE Transactions on Rehabilitation Engineering; bearing a date of Jun. 2000; pp. 198-202; vol. 8, No. 2; IEEE.

Kobetic, Rudi; Triolo, Ronald J.; Uhlir, James P.; Bieri, Carole; Wibowo, Michael; Polando, Gordie; Marsolais, E. Byron; Davis Jr., John A.; Ferguson, Kathleen A.; Sharma, Mukut; "Implanted Functional Electrical Stimulation System for Mobility in Paraplegia: A Follow-Up Case Report"; IEEE Transactions on Rehabilitation Engineering; bearing a date of Dec. 1999; pp. 390-398; vol. 7, No. 4; IEEE.

Krueger, Curtis; "New light on blood testing"; Oct. 20, 2006; pp. 1-2; St. Petersburg Times; printed on Oct. 24, 2006; located at http://www.sptimes.com/2006/10/20news_pf/Tampabay/New_light_on_blood_te.shtml.

Langer, Robert; Peppas, Nicholas A.; Advances in Biomaterials, Drug Delivery, and Bionanotechnology;; AIChE Journal—Bioengineering, Food, and Natural Products; Dec. 2003; pp. 2990-3006; vol. 49, No. 12.

Loeb, G.E.; Peck, R.A.; Martyniuk, J.; "Toward the Ultimate Metal Microelectrode"; Journal of Neuroscience Methods; bearing a date of 1995; pp. 175-183; vol. 63; Elsevier Science B.V.

Loeb, Gerald E.; Peck, Raymond A.; Moore, William H.; Hood, Kevin; "BION System for Distributed Neural Prosthetic Interfaces"; Medical Engineering and Physics; bearing a date of 2001; pp. 9-18; vol. 23; Elsevier Science Ltd.; located at: www.elsevier.com/locate/medengphy.

Lu, Zhao; Martel, Sylvain; "Preliminary Investigation of Bio-carriers Using Magnetotactic Bacteria"; Proceedings of the 28$^{th}$ IEEE EMBS Annual International Conference; bearing dates of Aug. 30, 2006-Sep. 3, 2006 and 2006; pp. 3415-3418; IEEE.

Mangan, Elizabeth V.; Kingsley, Dan A.; Quinn, Roger D.; Chiel, Hillel J.; "Development of a Peristaltic Endoscope"; IEEE International Conference on Robotics & Automation 2002; pp. 1-6; located at http://biorobots.cwru.edu/publications/ICRA02_Mangan_Endoscope.pdf.

Marks, William B.; Loeb, Gerald E.; "Action Currents, Internodal Potentials, and Extracellular Records of Myelinated Mammalian Nerve Fibers Derived from Node Potentials"; Biophysical Journal; 1976; pp. 655-668; vol. 16.

Martel, Sylvain; "Towards MRI-Controlled Ferromagnetic and MC-1 Magnetotactic Bacterial Carriers for Targeted Therapies in Arteriolocapillar Networks Stimulated by Tumoral Angiogenesis"; Proceedings of the 28$^{th}$ IEEE EMBS Annual International Conference; bearing dates of Aug. 30, 2006-Sep. 3, 2006 and 2006; pp. 3399-3402; IEEE.

Martel, Sylvain; Mathieu, Jean-Baptiste; Felfoul, Ouajdi; Chanu, Arnaud; Aboussouan, Eric; Tamaz, Samer; Pouponneau, Pierre; "Automatic Navigation of an Untethered Device in the Artery of a Living Animal using a Conventional Clinical Magnetic Resonance Imaging System"; Applied Physics Letters; 2007; pp. 114105-1-114105-3; vol. 90, No. 114105; American Institute of Physics.

Mathieu, J-B.; Martel, S.; Yahia, L'H.; Soulez, G.; Beaudoin, G.; "MRI Systems as a Mean of Propulsion for a Microdevice in Blood Vessels"; bearing a date of 2003; pp. 3419-3422; IEEE.

Matsui, Takemi; Matsumura, Kouji; Hagisawa, Kousuke; Ishihara, Masayuki; Ishizuka, Toshiaki; Suzuki, Minoru; Kurita, Akira; Kikuchi, Makoto; "A Novel Ferromagnetic Thermo-Stent for Plaque Stabilization That Self-Regulates the Temperature"; IEEE Transactions on Biomedical Engineering; bearing dates of Jun. 2002 and 2002; pp. 621-623; vol. 49, No. 6; IEEE.

McNeal, Donald R.; "Analysis of a Model for Excitation of Myelinated Nerve"; IEEE Transactions on Biomedical Engineering; bearing a date of Jul. 1976; pp. 329-337; vol. BME-23, No. 4.

Meier, P.; Oberthür, S.; Lang, M.; "Development of a compliant device for minimally invasive surgery"; Proceedings of the 28$^{th}$ IEEE EMBS Annual International Conference; bearing dates of Aug. 30, 2006-Sep. 3, 2006 and 2006; pp. 331-334; IEEE.

"MEMS at the cutting edge®, Patent Pending"; VERIMETRA; pp. 1-2; located at http://www.verimetra.com/flow.htm; printed on May 4, 2006.

Menciassi, A.; Park, Jong H.; Lee, S.; Gorini, S.; Dario, P.; Park, Jong-oh; "Robotic Solutions and Mechanisms for a Semi-Autonomous Endoscope"; Proceedings of the 2002 IEEE/RSJ International Conference on Intelligent Robots and Systems; bearing a date of 2002; pp. 1379-1384; IEEE.

Mohseni, Kamran; "Biomimetic & Bio-Inspired Aerial and Underwater Vehicles"; bearing a date of Sep. 23, 2006; pp. 1-10; printed on Jan. 4, 2007; located at http://enstrophy.colorado.edu/~mohseni/MicroVehicles1.html#UUV1#UUV1.

Mosse, Charles; Mills, Tim; Appleyard, Mark; Swain, Paul; "Electrostimulation to move endoscopes in the small bowel"; Proceedings of SPIE; bearing a date of 2001; pp. 24-28; vol. 4158.

Murthy, S. Narasimha; Hiremath, Shobha Rani R.; "Physical and Chemical Permeation Enhancers in Transdermal Delivery of Terbutaline Sulphate"; AAPS PharmSciTech; bearing a date of 2001; pp. 1-5; vol. 2001, 2(1); Technical Note 1; located at http://www.pharmscitech.com/.

Nakayama, Yasuhide; Ji-Youn, Kim; Nishi, Shogo; Ueno, Hikaru; Matsuda, Takehisa; "Development of high-performance stent: gelatinous photogel-coated stent that permits drug delivery and gene transfer"; J Biomed Mater Res; bearing dates of Nov. 13, 2000, Apr. 23, 2001, May 10, 2001 and 2001; pp. 559-566; vol. 57; John Wiley & Sons, Inc.

Naqvi, Nasir H.; Rudrauf, David; Damasio, Hanna; Bechara, Antoine; "Damage to the Insula Disrupts Addiction to Cigarette Smoking"; Science; bearing a date of Jan. 26, 2007; pp. 531-534; vol. 315, No. 531; located at: www.sciencemag.org; printed on Jan. 25, 2007.

Neto, A.M. Figueiredo; Godinho, M.H.; Toth-Katona, T.; Palffy-Muhoray, P.; "Optical, Magnetic and Dielectric Properties of Non-Liquid Crystalline Elastomers Doped with Magnetic Colloids"; Brazilian Journal of Physics; Bearing a date of Mar. 2005; pp. 184-189; vol. 35, No. 1.

"New Medical Device Combines Wireless and MEMS Technology"; Georgia Institute of Technology; pp. 1-4; PhysOrg.com; located at: http://www.physorg.com/printnews.php?newsid=10533; printed on Feb. 20, 2006.

Nieuwenhuizen-Berkovits, P.; "lubrelastic medical appliances"; Lubrelastic Medical Appliances; pp. 1-4; located at: http://www.xs4all.nl/~plieno070/caeng.html; printed on Feb. 20, 2006.

Nyitrai, Zsolt; Illyefalvi-Vitéz, Zsolt; Pinkola, János; "Preparing Stents with Masking & Etching Technology"; 26$^{th}$ International Spring Seminar on Electronics Technology; bearing dates of May 8, 2003-May 11, 2003 and 2003; pp. 321-324; IEEE.

Olsson III, R.H.; Gulari, M.N.; Wise, K.D.; "Poster 114: Silicon Neural Recording Arrays with On-Chip Electronics for In-Vivo Data Acquisition"; Microtechnologies in Medicine and Biology; bearing dates of May 2, 2002-May 4, 2002; pp. 237-240; IEEE.

Oweiss, Karim G.; Anderson, David J.; "A New Technique for Blind Source Separation Using Subband Subspace Analysis in Correlated Multichannel Signal Environments"; bearing a date of 2001; pp. 2813-2816; IEEE.

Patronik, N.A.; Ota, T.; Zenati, M.A.; Riviere, C.N.; "Improved Traction for a Mobile Robot Traveling on the Heart"; Proceedings of the 28$^{th}$ IEEE EMBS Annual International Conference; bearing dates of Aug. 30, 2006-Sep. 3, 2006 and 2006; pp. 339-342; IEEE.

Peckham, P. Hunter; Knutson, Jayme S.; "Functional Electrical Stimulation for Neuromuscular Applications"; Annual Review Biomedical Engineering; bearing a date of 2005; pp. 327-360; vol. 7; Annual Reviews.

Rattay, F.; "The Basic Mechanism for the Electrical Stimulation of the Nervous System"; Neuroscience; 1999; pp. 335-346; vol. 98. No. 2; Elsevier Science Ltd; printed on Mar. 15, 2007.

Rattay, Frank, Aberham, Matthias; "Modeling Axon Membranes from Functional Electrical Stimulation"; IEEE Transactions on Biomedical Engineering; bearing a date of Dec. 1993; pp. 1201-1209; vol. 40, No. 12; IEEE.

Rattay, Frank; "Analysis of Models for Extracellular Fiber Stimulation"; IEEE Transactions on Biomedical Engineering; bearing a date of Jul. 1989; pp. 676-682; vol. 36, No. 7; IEEE.

"Remote-Control Electrostimulation Capsule"; Popular Science; bearing dates of 2002 and 2003; pp. 1-2; located at http://www.popsci.com/popsci/brown/2003/article/0.18881.537028.00.html; printed on May 4, 2006.

"Researchers: Squid-Inspired Vortex Generators Could Mean Better Propulsion for Unmanned Underwater Vehicles"; UnderwaterTimes.com; Dec. 12, 2006; pp. 1-2; UnderwaterTimes.com; printed on Jan. 4, 2007; located at http://www.underwatertimes.com/print.php?article_id=51030782641.

Rice, Mike; "Implantable Neurostimulation Device Market Poised for Explosive Growth"; Future Fab International; Jan. 7, 2006; pp. 1-4; printed on Oct. 6, 2006; located at http://www.future-fab.com/documents.asp?d_ID=3725.

Rice, Mike; "New Products, Emphasis on Miniaturization Driving Medical Device Innovation"; bearing a date Aug. 23, 2006; pp. 1-3; Advantage Business Media; located at http://www.mdtmag.com/scripts/ShowPR.asp?PUBCODE=046&ACCT=0006109&ISSUE=0603&RELTYPE=PR&PRODCODE=0790&PRODLETT=A; printed on Aug. 23, 2006.

Riedmüller, J.; Bolz, A.; Rebling, H.; Schaldach, M.; "Improvement of Stimulation and Sensing Performance of Bipolar Pacemaker Leads"; IEEE Eng. Med. Biol. Soc.; 1992; pp. 2364-2365; IEEE.

Robinson, David A.; "The Electrical Properties of Metal Microelectrodes"; Proceedings of the IEEE; bearing a date of Jun. 1968; pp. 1065-1071; vol. 56, No. 6.

Rousche, Patrick J.; Pellinen, David S.; Pivin, David P.; Williams, Justin C.; Vetter, Rio J.; Kipke, Daryl R.; "Flexible Polyimide-Based Intracortical Electrode Arrays with Bioactive Capability"; IEEE Transactions on Biomedical Engineering; bearing a date Mar. 2001; pp. 361-371; vol. 48, No. 3; IEEE.

Rutten, Wim; Mouveroux, Jean-Marie; Buitenweg, Jan; Heida, Ciska; Ruardij, Teun; Marani, Enrico; Lakke, Egbert; "Neuroelectronic Interfacing with Cultured Multielectrode Arrays Toward a Cultured Probe"; Proceedings of the IEEE; bearing a date of Jul. 2001; pp. 1013-1029; vol. 89, No. 7; IEEE.

Saltzman, John R.; "Endoscopic Advances—A View Toward the Future"; bearing dates of May 4, 2006, May 17, 2005, and 2005; pp. 1-4; Medscape; located at http://www.medscape.com/viewarticle/505100; printed on May 4, 2006.

Schmidt, W.; Behrens, P.; Behrend, D.; Schmitz, K.-P.; Andresen, R.; "Experimental Study of Peripheral, Balloon-expandable Stent Systems"; Progress in Biomedical Research; bearing a date of May 2001; pp. 246-255.

Schoonhoven, R.; Stegeman, D.F.; "Models and Analysis of Compound Nerve Action Potentials"; Critical Reviews in Biomedical Engineering; bearing a date of 1991; pp. 47-111; vol. 19, No. 1; CRC Press, Inc.

Senel, Sevda; Hincal, A. Atilla; "Drug permeation enhancement via buccal route: possibilities and limitations"; Journal of Controlled Release; bearing a date of 2001; pp. 133-144; vol. 72 (2001); Elsevier; located at www.elsevier.com/locate/jconrel.

Serruya, Mijail D.; Hatsopoulos, Nicholas G.; Paninski, Liam; Fellows, Matthew R.; Donoghue, John P.; "Brief Communications: Instant Neural Control of a Movement Signal"; Nature; bearing a date of Mar. 14, 2002; pp. 141-142; vol. 416; Macmillan Magazines Ltd; located at: www.nature.com.

Serruys, Patrick W.; Kutryk, Michael J.B.; Ong, Andrew T.L.; "Coronary-Artery Stents"; The New England Journal of Medicine; bearing dates of Feb. 2, 2006 and Feb. 15, 2006; pp. 483-495; vol. 354;5; Massachusetts Medical Society.

Shabalovskaya, Svetlana, A.; "Surface, corrosion and biocompatibility aspects of Nitinol as an implant material"; Bio-Medical Materials and Engineering; bearing dates of Apr. 4, 2001, and 2002; pp. 69-109; vol. 12; IOS Press.

Shahinpoor, Mohsen; Kim, Kwang J.; Ionic polymer-metal composites: IV. Industrial and medical applications; Smart Materials and Structures; 2005; pp. 197-214; vol. 14; Institute of Physics Publishing.

Smith, Michael; "PAS: Nasal Spray Flu Vaccine Seems Safe and Effective in Young"; May 2, 2006; pp. 1-2; MedPage Today, LLC; bearing dates of 2004-2006; printed on May 4, 2006; located at http://www.medpagetoday.com/tbprint.cfm?tbid=3213.

Snoek, GJ; Ijzerman, MJ; In 'T Groen, Facg; Stoffers, TS; Zilvold, G; "Use of the NESS Handmaster to Restore Handfunction in Tetraplegia: Clinical Experiences in Ten Patients"; Spinal Cord; bearing a date of 2000; pp. 244-249; vol. 38; International Medical Society of Paraplegia.

Snow, E.S.; Perkins, F.K.; Houser, E.J.; Badescu, S.C.; Reinecke, T. L.; "Chemical Detection with a Single-Walled Carbon Nanotube Capacitor"; Science; Mar. 25, 2005; pp. 1942-1945; vol. 307; www.sciencemag.org.

Stoeckel, Dieter; Pelton, Alan; Duerig, Tom; "Self-expanding nitinol stents: material and design considerations"; European Radiology; bearing dates of Jan. 28, 2003, May 22, 2003, Jul. 1, 2003, Sep. 3, 2003, Feb. 2004 and 2004; pp. 292-301(1-2); vol. 14, No. 2; Springer-Verlag GmbH-SpringerLink—Article; located at: http://www.springerlink.com/(1begg455gtgifseqqptyb43m)/app/home/contribution.asp?referrer=parent&backto=issue.17.26.journal.27.147:browsepublicationsresults.444.1551; printed on Feb. 22, 2006.

Strauss, Bradley H., M.D., Ph.D.; Li, Chris, M.D.; Whittingham, Heather A., M.Sc; Tio, Fermin O., M.D.; Kutryk, Michael J.B., M.D., Ph.D.; Janicki, Christian, Ph.D.; Sparkes, John, D., M.Sc.; Turnlund, Todd, B.Sc.; Sweet, William L., M.D.; "Late Effects of Low-Energy Gamma-Emitting Stents in a Rabbit Iliac Artery Model"; Int. J. Radiation Oncology Biol. Phys.; bearing dates of Oct. 23, 2001, May 13, 2002 and May 15, 2002 and 2002; pp. 551-561; vol. 54, No. 2; Elsevier Science Inc.

Struijk, Johannes Jan; "The Extracellular Potential of a Myelinated Nerve Fiber in an Unbounded Medium and in Nerve Cuff Models"; Biophysical Journal; bearing a date of Jun. 1997;'pp. 2457-2469; vol. 72; Biophysical Society.

Taylor, Dawn M.; Helms Tillery, Stephen I.; Schwartz, Andrew B.; "Research Article: Direct Cortical Control of 3D Neuroprosthetic Devices"; Science; bearing a date of Jun. 7, 2002; pp. 1829-1832; vol. 296; located at: www.sciencemag.org.

"Tiny Robot Reduces Need for Surgery"; Pink Tentacle; bearing a date of Feb. 26, 2007; p. 1; located at http://www.pinktentacle.com/2007/02/tiny-robot-reduces-need-for-surgery; printed on Mar. 8, 2007.

"Trying to control pain can be a double-edged sword, say scientists"; PhysOrg.com; printed on Nov. 2, 2006; pp. 1-2; located at http://www.physorg.com/printnews.php?newsid=81599312.

Tummala, R. Lal; Mukherjee, R.; Aslam, D.; Xi, Ning; Mahadevan, S.; Weng, J.; "Reconfigurable Adaptable Micro-robot"; IEEE; bearing a date of 1999; pp. 687-691.

Twardoch, U.M.; "Integrity of Ultramicro-Stimulation Electrodes Determined from Electrochemical Measurements"; Journal of Applied Electrochemistry; bearing a date of 1994; pp. 835-857; vol. 24; Chapman & Hall.

Warland, David K.; Reinagel, Pamela; Meister, Markus; "Decoding Visual Information from a Population of Retinal Ganglion Cells"; bearing a date of 1997; pp. 2336-2350; The American Physiological Society.

Weis, Rolf; Müller, Bernt; Fromherz, Peter; "Neuron Adhesion on a Silicon Chip Probed by an Array of Field-Effect Transitors"; Physical Review Letters; bearing a date of Jan. 8, 1996; pp. 327-330; vol. 76, No. 2; The American Physical Society.

Wessberg, Johan; Stambaugh, Christopher R.; Kralik, Jerald D.; Beck, Pamela D.; Laubach, Mark; Chapin, John K.; Kim, Jung; Biggs, S. James; Srinivasan, Mandayam A.; Nicolelis, Miguel A.L.; "Letters to Nature: Real-Time Prediction of Hand Trajectory by Ensembles of Cortical Neurons in Primates"; Nature; bearing a date of Nov. 16, 2000; pp. 361-365; vol. 408; Macmillan Magazines Ltd; located at: www.nature.com.

White, Dave; "Mini Robot Explores, Gives you Medicine from Within"; Mobile Magazine; bearing a date of Feb. 27, 2007; p. 1; located at: http://www.mobilemag.com/content/100/313/C11869/; printed on Mar. 8, 2007.

Yusa, Go; Muraki, Koji; Takashina, Kei; Hashimoto, Katsushi; Hirayama, Yoshiro; "Controlled multiple quantum coherences of nuclear spins in a nanometre-scale device"; Nature; Apr. 21, 2005; pp. 1001-1005; vol. 434; 2005 Nature Publishing Group; www.nature.com/nature.

"Zyvex NanoEffector Microgrippers"; Nanotechnology at Zyvex; printed on Dec. 7, 2006; pp. 1-2; located at http://www.zyvex.com/Products/Grippers_Features.html.

"Zyvex NanoEffector Microgrippers"; Zyvex.com; bearing a date of 2006; pp. 1-2; Zyvex Corporation.

U.S. Appl. No. 13/136,680, Publication Date Aug. 5, 2011, Ferren et al.

U.S. Appl. No. 13/136,679, Publication Date Aug. 5, 2011, Ferren et al.

U.S. Appl. No. 13/136,677, Publication Date Aug. 5, 2011, Ferren et al.

U.S. Appl. No. 13/136,676, Publication Date Aug. 5, 2011, Ferren et al.

U.S. Appl. No. 13/136,675, Publication Date Aug. 5, 2011, Ferren et al.

U.S. Appl. No. 13/136,678, Publication Date Aug. 5, 2011, Ferren et al.

U.S. Appl. No. 13/136,674, Publication Date Aug. 5, 2011, Ferren et al.

Arkin, Ronald C.; "Towards the Unification of Navigational Planning and Reactive Control"; Working Notes of the AAAI Spring Symposium on Robot Navigation; bearing dates of Mar. 20-28, 1989; pp. 1-6.

Arleo et al.; "Spatial Cognition and Neuro-Mimetic Navigation: A Model of Hippocampal Place Cell Activity"; bearing a date of Oct. 28, 1999; pp. 1-13.

Balakrishnan et al.; "Spatial Learning and Localization in Rodents: A Computational Model of the Hippocampus and its Implications for Mobile Robots"; Adaptive Behavior; bearing a date of 1999; pp. 173-216 plus cover page; vol. 7, No. 2; SAGE Publications.

Bellin et al.; "Polymeric triple-shape materials"; PNAS; bearing dates of Nov. 18, 2006 and 2006; pp. 18043-18047; vol. 103, No. 48; The National Academy of Sciences of the USA; located at www.pnas.org/cgi/doi/10,1073/pnas.0608586103.

Berman et al.; "Decentralized Autonomous AGV System for Material Handling"; iFirst; bearing a date of Oct. 2002; pp. 3995-4006 (Only the Abstract is being provided); vol. 40, No. 15; located at: http://www.informaworld.com/smpp/content~content=a713846479~db=ai; printed on Apr. 24, 2007.

Bianco et al.; "Carbon Nanotube-based Vectors for Delivering Immunotherapeutics and Drugs"; Nanotechnologies for the Live Sciences: Nanomaterials for Medical Diagnosis and Therapy; bearing a date of 2007; Chapter 3; pp. 85-142.; vol. 10; WILEY-VCH Verlag GmbH & Co. KGaA; Weinheim.

Breslin et al.; "Autofluorescence and Diffuse Reflectance Properties Malignant and Benign Breast Tissues"; Annals of Surgical Oncology; bearing dates of 2003 and 2004; pp. 65-70; vol. 11, No. 1; Lippincott Williams & Wilkin.

Bright et al.; "Automated Pipe Inspection Robot"; Industrial Robot: An International Journal; bearing a date of Aug. 1997; pp. 285-289 (Only the Abstract is being provided); vol. 24, No. 4; located at: http://www.emeraldinsight.com/10.1108/01439919710176372; printed on Apr. 23, 2007.

Brinn, David; "A incredible journey from an Israeli robotics team"; ISRAEL21c: A Focus Beyond; bearing a date of Nov. 12, 2006; pp. 1-3; ISRAEL21c.org.

Brown et al.; "Performance Test Results of an Integrated GPS/MEMS Inertial Navigation Package"; Proceedings of ION GNSS 2004, bearing a date of Sep. 2004; pp. 1-8.

Budgett et al.; "Novel technology for the provision of power to implantable physiological devices"; Journal of Applied Physiology; bearing dates of Jan. 27, 2006, Jan. 5, 2007, and 2007; pp. 1658-1663; vol. 102; The American Physiological Society.

Bullitt et al.; "Analysis of Time-Varying Images Using 3D Vascular Models"; Proceedings 30th Applied Imagery Pattern Recognition Workshop; bearing a date of Apr. 2001; pp. 9-14; IEEE Computer Society; Piscataway, NJ.

Burke et al.; "Towards a single-chip, implantable RFID system: is a single-cell radio possible?"; Biomed Microdevices; bearing a date of 2009; pp. 1-8; Springer.

Cady et al.; "Optimized linkage and quenching strategies for quantum dot molecular beacons"; Molecular and Cellular Probes; bearing dates of Jul. 5, 2006, Sep. 7, 2006, Sep. 17, 2006, 2006, and 2007; pp. 116-124; vol. 21; Elsevier Ltd.

Cavalcanti et al.; "Autonomous Multi-Robot Sensor-Based Cooperation for Nanomedicine"; Nanotechnology Special Edition; bearing a date of Aug. 2002; pp. 1-4; International Journal of Nonlinear Science and Numerical Stimulation.

Chen et al.; "Review on the Achievements in Simultaneous Localization and Map Building for Mobile Robot" CSA Illumina; bearing a date of Jun. 2005; pp. 455-460 (Only the Abstract is being provided); vol. 22, No. 3; ProQuest-CSA LLC; located at: http://md1.csa.com/partners/viewrecord.php?requester=gs&collection=TRD&recid=A053654818AH&recid=2005134422784EA&q=Review+on+the+Achievements+in+Simultaneous+Localization+and+Map+Building+for+Mobile+Robot&uid=790366044&setcookie=yes.

Chiyo et al.; "Effective detection of bronchial preinvasive lesions by a new autofluorescence imaging bronchovideoscope system"; Lung Cancer; bearing dates of May 12, 2004, Nov. 17, 2004, Nov. 23, 2004, 2004, and 2005; pp. 307-313; vol. 48; Elsevier Ireland Ltd.

Chung et al.; "Advanced Optical Imaging Requiring No Contrast Agents-A New Armamentarium for Medicine and Surgery"; Current Surgery; bearing dates of May/Jun. 2005 and 2005; pp. 365-370; vol. 62, No. 3; Elsevier Inc.

Dacosta et al.; "Autofluorescence characterisation of isolated whole crypts and primary cultured human epithelial cells from normal, hyperplastic, and adenomatous colonic mucosa"; Journal of Clinical Pathology; bearing dates of 2004 and 2005; pp. 766-774; vol. 58.

Degani et al.; "Minimalistic, Dynamic, Tube Climbing Robot"; 2010 IEEE International Conference on Robotics and Automation; bearing dates of May 3-8, 2010 and 2010; pp. 1100-1101; IEEE.

Desouza et al.; "Vision for Mobile Robot Navigation: A Survey"; IEEE Transactions on Pattern Analysis and Machine Intelligence; bearing a date of Feb. 2002; pp. 237-267 (Only the Abstract is being provided); vol. 24, No. 2; located at: http://csdl2.computer.org/persagen/DLAbsToc.jsp?resourcePath=/dl/trans/tp/&toc=comp/trans/tp/2002/02/i2toc.xml&DOI=10.1109/34.982903; printed on Apr. 23, 2007.

Diard et al.; "A theoretical comparison of probabilistic and biomimetic models of mobile robot navigation"; Proceedings of the 2004 IEEE International Conference on Robotics & Automation; bearing dates of Apr. 2004 and 2004; pp. 933-938; IEEE.

Dweik et al.; "Exhaled breath analysis: the new frontier in medical testing"; Journal of Breath Research; bearing a date of 2008; pp. 1-3; vol. 2; IOP Publishing Ltd; UK.

Edwards, Lin; "Spider pill to seek out disease"; PhysOrg.com; bearing dates of Oct. 16, 2009 and 2009; p. 1.

Eker et al.; "Clinical spectral characterisation of colonic mucosal lesions using autofluorescence and δaminolevulinic acid sensitization"; Gut; bearing dates of 1998 and 1999; pp. 511-518; vol. 44.

Eulenstein et al.; "Ultrasound-Based Navigation System Incorporating Preoperative Planning for Liver Surgery"; International Congress Series CARS 2004—Computer Assisted Radiology and Surgery, Proceedings of the 18th International Congress and Exhibition; bearing a date of 2004; pp. 758-763; vol. 1268.

Filliat et al.; "Map Based Navigation in Mobile Robots: I. A Review of Localization Strategies"; Science Direct-Cognitive Systems Research; bearing dates of Feb. 12, 2003 and Dec. 2003; pp. 1-58; vol. 4, No. 4; Elsevier Science.

Foxlin et al.; "Miniature 6-DOF inertial system for tracking HMDs"; Helmet and Head-Mounted Displays III, AeroSense 98; bearing dates of Apr. 13-14, 1998; pp. 1-15; vol. 3362; SPIE.

Gabrecht et al.; "Detection of early bronchial cancer by autofluorescence: results in patients with H&N cancer"; Diagnostic Optical Spectroscopy in Biomedicine IV, Proc. SPIE-OSA Biomedical Optics; bearing a date of 2007; pp. 1-8; vol. 6628; SPIE-OSA.

Gao et al., "A Micro Sensing Probe for Detecting Individual Biological Cells"; Proceedings of the 25$^{th}$ Annual International Conference of the IEEE EMBS; bearing dates of Sep. 17-21, 2003 and 2003; pp. 3348-3351; IEEE.

Gillenwater et al.; "Noninvasive Diagnosis of Oral Neoplasia Based on Fluorescence Spectroscopy and Native Tissue Autofluorescence"; Archives of Otolaryngology-Head & Neck Surgery; bearing a date of Nov. 1998 and 1998; pp. 1251-1258; vol. 124.

Grifantini, Kristina; "Voyage of the Bacteria Bots"; Technology Review; bearing a date of Oct. 31, 2008; pp. 1-4; Technology Review.

Groothuis et al.; "The entry of antiviral and antiretroviral drugs into the central nervous system"; Journal of NeuroVirology; bearing a date of 1997; pp. 387-400; vol. 3; Journal of NeuroVirology, Inc.

"Guessing Robots Predict Their Environments, Navigate Better"; PhysOrg.com; printed on Sep. 16, 2008; pp. 1-2; original story found at www.phyorg.com/news100887209.html.

Gur, Amir; "The Nanobots are Coming"; TFOT; bearing a date of Jul. 9, 2007; pp. 1-2; The Future of Things.

Hattori, Kevin; "Robot Can Crawl Through Human Body"; American Technion Society; bearing a date of Jul. 7, 2009; pp. 1-2; American Technion Society; located at http://www.ats.org/site/News2?page=NewsArticle&id=6063&news_iv_ctrl=1161&printer_friendly=1.

Herth et al.; "Successful Bronchoscopic Placement of Tracheobronchial Stents Without Fluoroscopy*"; Chest; bearing a date of Jun. 2001; pp. 1910-1912; vol. 119, No. 6; American College of Chest Physicians.

Hertzberg et al.; "Landmark-Based Autonomous Navigation in Sewerage Pipes"; Proceedings of EUROBOT; bearing a date of 1996; pp. 68-73; IEEE.

Hirsch et al.; "A new device with PZT ultrasonic transducers in MEMS technology"; Journal of Physics: Conference Series 34, International MEMS Conference 2006; bearing a date of 2006; pp. 475-480; IOP Publishing Ltd.

Hollings et al.; "Diagnostic imaging of lung cancer"; European Respiratory Journal; bearing a date of 2002, pp. 722-742; vol. 19; ERS Journals Ltd.

Hornyak, Tim; "RFID Powder"; Scientific American Magazine; bearing dates of Feb. 2008 and 2008; pp. 68-71; Scientific American, Inc.

Hosseini-Khayat, Saied; "A Lightweight Security Protocol for Ultralow Power ASIC Implementation for Wireless Implantable Medical Devices"; 2011 Symposium on Medical Information and Communication Technology (ISMICT); bearing dates of 2011 and Mar. 27-30, 2011; pp. 6-9; IEEE.

Howell et al.; "Practical Mobile Robot Self-Localization"; Proceedings of the IEEE International Conference on Robotics and Automation, 2000; bearing dates of Apr. 24-28, 2000; pp. 3485-3492; vol. 4.

Jaiswal et al.; "Long-term multiple color imaging of live cells using quantum dot bioconjugates"; Nature Biotechnology; bearing dates of Jan. 2003 and 2003; pp. 47-51; vol. 21; Nature Publishing Group.

Jovanov et al.; "A wireless body area network of intelligent motion sensors for computer assisted physical rehabilitation"; Journal of NeuroEngineering and Rehabilitation; bearing dates of Mar. 1, 2005, Jan. 28, 2005, Mar. 1, 2005, and 2005; pp. 1-10; vol. 2, No. 6; BioMed Central Ltd.

Karino et al.; "Flow Patterns in Vessels of Simple and Complex Geometriesa$^a$"; Annals of the New York Academy of Sciences; bearing a date of 1987; pp. 422-441; vol. 516.

Kawaguchi et al.; "Internal Pipe Inspection Robot"; IEEE Xplore; bearing dates of May 21, 1995-May 27, 1995 and 2005; pp. 857-862 (Only the Abstract is being provided); vol. 1; IEEE; located at: http://ieeexplore.ieee.org/xpls/abs_all.jsp?rnumber=525390; printed on Apr. 23, 2007.

Kharitonov et al.; "Exhaled Markers of Pulmonary Disease"; American Journal of Respiratory and Critical Care Medicine; bearing dates of Sep. 5, 2000, Jan. 24, 2001, and 2001; pp. 1693-1722; vol. 163.

Kim et al.; "Inchworm-Like Microbot for Capsule Endoscope"; Proceedings of the 2004 IEEE International Conference on Robotics and Biomimetics; bearing dates of Aug. 22-26, 2004 and 2004; pp. 458-463; IEEE.

Kim et al.; "Ultrasensitive carbon nanotube-based biosensors using antibody-binding fragments"; Analytical Biochemistry; bearing a date of 2008; pp. 193-198; vol. 381; Elsevier Inc.

Kirchner et al.; "A Prototype Study of an Autonomous Robot Platform for Sewerage System Maintenance"; Autonomous Robots; bearing a date of 1997; pp. 319-331; vol. 4; Kluwer Academic Publishers.

Kitaoka et al.; "A three-dimensional model of the human airway tree"; Journal of Applied Physiology; bearing a date of 1999; pp. 2207-2217; vol. 87; The American Physiological Society.

Kitching, John; "Time for a Better Receiver: Chip-Scale Atomic Frequency References"; GPS World; bearing a date of Nov. 2007; pp. 52-57.

Knappe, Svenja; "Emerging Topics: Mems Atomic Clocks"; Comprehensive Microsystems; bearing a date of 2007; pp. 571-612; vol. 3; Elsevier B.V.; Netherlands.

Koenig et al.; "Laser-Induced Autofluorescence for Medical Diagnosis"; Journal of Fluorescence; bearing a date of 1994, pp. 17-40; vol. 4, No. 1; Plenum Publishing Corporation.

Kuipers et al.; "A Robot Exploration and Mapping Strategy Based on a Semantic Hierarchy of Spatial Representations"; Robotics and Autonomous Systems; bearing a date of 1981; pp. 47-63; vol. 8; Elsevier Science Publishers B.V.

Kuntze et al.; "Experiences With the Development of a Robot for Smart Multisensoricpipe Inspection"; IEEE Xplore; bearing dates of May 16, 1998-May 20, 1998 and 2005; pp. 1773-1778 (Only the Abstract is being provided); vol. 2; IEEE; located at: http://ieeexplore.ieee.org/xpls/abs_all.jsp?rnumber=677423; printed on Apr. 23, 2007.

Latombe, Jean-Claude; "Chapter 1: Introduction and Overview"; Robot Motion Planning; bearing a date of 1991; 11 pages total, pp. 12-20; Kluwer Academic Publishers.

Laumond et al.; "Robot Motion Planning and Control"; bearing a date of 1998; pp. 1-343 plus cover page, foreword and table of contents (353 total pages); Springer.

Leong et al.; "Tetherless thermobiochemically actuated microgrippers"; PNAS; bearing dates of Jan. 20, 2009 and 2009; pp. 703-708; vol. 106, No. 3; The National Academy of Sciences of the USA; located at www.pnas.org_cgi_doi_10.1073_pnas.0807699106.

Luckevich, Mark, "MEMS microvalves: the new valve world"; Valve-World; bearing a date of May 2007; pp. 79-83.

Lynch et al.; "Design of Piezoresistive MEMS-Based Accelerometer for Integration with Wireless Sensing Unit for Structural Monitoring"; Journal of Aerospace Engineering; bearing a date of Jul. 2003; pp. 108-114; vol. 3; ASCE.

Machado et al., "Detection of Lung Cancer by Sensor Array Analyses of Exhaled Breath"; American Journal of Respiratory and Critical Care Medicine; bearing a date of 2005; pp. 1286-1291; vol. 171.

Marcu et al.; "In vivo detection of macrophages in a rabbit atherosclerotic model by time-resolved laser-induced fluorescence spectroscopy"; Atherosclerosis; bearing a date of 2005, pp. 295-303; vol. 181; Elsevier Ireland Ltd.

Martel, Sylvain; "Fundamental Principles and Issues of High-speed Piezoactuated Three-legged Motion for Miniature Robots Designed for Nanometer-scale Operations"; The International Journal of Robotics Research; bearing dates of Jul. 2005 and 2005; pp. 575-588; vol. 24, No. 7; Sage Publications.

Mataric, Maja J.; "Integration of Representation into Goal-Driven Behavior-Based Robots"; IEEE Transactions on Robotics and Automation; bearing dates of Jun. 1992 and 1992; pp. 304-312; vol. 8, No. 3; IEEE.

Mattley et al.; "Blood Characterization using uv/vis Spectroscopy"; Advances in Fluorescence Sensing Technology II (Proceedings Volume); bearing a date of 1995; pp. 462-470; vol. 2388; SPIE.

Mehmood et al.; "Autonomous Navigation of Mobile Agents Using RFID-Enabled Space Partitions"; ACMGIS'08; bearing dates of Nov. 5-7, 2008 and 2008; pp. 1-10; ACM.

Menciassi et al.; "Towards Active Capsular Endoscopy: Preliminary Results on a Legged Platform"; Proceedings of the 28th IEEE EMBS Annual International Conference; bearing dates Aug. 30, 2006-Sep. 3, 2006 and 2006; pp. 2215-2218; IEEE.

Meyer et al.; "Map-Based Navigation in Mobile Robots: II. A Review of Map-Learning and Path-Learning Strategies"; Science Direct-Cognitive Systems Research; bearing dates of Feb. 12, 2003 and Dec. 4, 2003; pp. 1-51; vol. 4, No. 4; Elsevier Science.

Mohan et al., "Bokode: Imperceptible Visual tags for Camera Based Interaction from a Distance"; ACM Transactions on Graphics (Proceedings of SIGGRAPH 2009); bearing dates of Aug. 3-7, 2009; pp. 1-8.

Mok et al.; "Recent Progress in Nucleic Acid Aptamer-Based Biosensors and Bioassays"; Sensors; bearing a date of 2008; pp. 7050-7084; vol. 8.

Morrison et al., "Clinical Applications of Micro- and Nanoscale Biosensors"; Biomedical Nanostructures; bearing a date of 2008; Chapter 17; pp. 433-454; John Wiley & Sons, Inc.

Motomiya et al., "Flow Patterns in the Human Carotid Artery Bifurcation"; Stroke; bearing dates of Jan.-Feb. 1984; pp. 50-56; vol. 15, No. 1.

Nehmzow et al.; "Robot Navigation in the Real World: Experiments with Manchester's *FortyTwo* in Unmodified, Large Environments"; Robotics and Autonomous Systems; bearing a date of 2000; pp. 223-242; vol. 33; Elsevier Science B.V.

Nguyen, Clark T.-C.; "MEMS Technology for Timing and Frequency Control"; IEEE Transactions on Ultrasonics, Ferroelectrics, and Frequency Controls; bearing dates of Feb. 2007 and 2007; pp. 251-270; vol. 54, No. 2; IEEE.

Nordstrom et al.; "Identification of Cervical Intraepithelial Neoplasia (CIN) Using UV-Excited Fluorescence and Diffuse-Reflectance Tissue Spectroscopy"; Lasers in Surgery and Medicine; bearing a date of 2001; pp. 118-127; vol. 29; Wiley-Liss, Inc.

Nowinski et al.; "Three-dimensional Atlas of the Brain Anatomy and Vasculature"; RadioGraphics; bearing dates of Jan.-Feb. 2005 and 2005; pp. 263-271; vol. 25, No. 1; RSNA.

Pan et al.; "A magnetically driven PDMS micropump with ball check-valves"; Journal of Micromechanics and Microengineering; bearing a date of 2005, pp. 1021-1026; vol. 15; IOP Publishing Ltd.

Pavlidis, N.; "The diagnostic and therapeutic management of leptomeningeal carcinomatosis"; Annals of Oncology; bearing a date of 2004; pp. iv285-iv291; vol. 15 (Supp. 4); European Society for Medical Oncology.

Peng et al.; "Ultraviolet light-emitting diodes operating in the 340 nm wavelength range and application to time-resolved fluorescence spectroscopy"; Applied Physics Letters; bearing dates of Aug. 23, 2004 and 2004; pp. 1436-1438; vol. 85, No. 8; American Institute of Physics.

Pfister et al.; "Weighted Line Fitting Algorithms for Mobile Robot Map Building and Efficient Data Representation"; Proceedings of the 2003 IEEE International Conference on Robotics and Automation; bearing a date of Sep. 14-19, 2003; pp. 1-8.

"Philips develops "intelligent pill""; Reuters; bearing a date of Nov. 11, 2008; p. 1; Thomson Reuters.

"Philips' intelligent pill targets drug development and treatment for digestive tract diseases"; PhysOrg.com; bearing a date of Nov. 11, 2008; pp. 1-3; located at http://www.physorg.com/news145640874.html.

Phillips et al.; "Detection of Lung Cancer With Volatile Markers in the Breath*"; Chest; bearing dates of Jun. 2003 and 2003; pp. 2115-2123; vol. 123, No. 6; American College of Chest Physicians.

Pisupati et al.; "A Central Axis Algorithm for 3D Bronchial Tree Structures"; Proceedings of the International Symposium on Computer Vision; bearing a date of 1995; pp. 259-264; IEEE.

Psathakis et al.; "8-Isoprostane, a Marker of Oxidative Stress, Is Increased in the Expired Breath Condensate of Patients With Pulmonary Sarcoidosis*"; Chest; bearing dates of Mar. 2004 and 2004, pp. 1005-1011; vol. 125, No. 3; American College of Chest Physicians.

Quaglia et al.; "An endoscopic capsule robot: a meso-scale engineering case study"; Journal of Micromechanics and Microengineering; bearing a date of 2009; pp. 1-11; vol. 19; IOP Publishing Ltd.

Quirini et al.; "Design of a Pill-Sized 12-legged Endoscopic Capsule Robot"; 2007 IEEE International Conference on Robotics and Automation; bearing dates of Apr. 10-14, 2007 and 2007; pp. 1856-1862; IEEE.

Raman et al.; "In Vivo Atherosclerotic Plaque Characterization Using Magnetic Susceptibility Distinguishes Symptom-Producing Plaques"; JACC: Cardiovascular Imaging; bearing dates of Jan. 2008 and 2008; pp. 49-57; vol. 1, No. 1; Elsevier.

Rasmussen et al.; "Proximity-based Access Control for Implantable Medical Devices"; CCS '09, Proceedings of the 16th ACM Conference on Computer and Communications Security; bearing dates of Nov. 9-13, 2009 and 2009; pp. 1-10.

"Remote-controlled capsule endoscope safely examines the stomach"; PhysOrg.com; bearing a date of Jan. 18, 2011; pp. 1-2; located at http://www.physorg.com/news-2011-01-remote-controlled-capsule-endoscope-safely-stomach.html.

"Researchers Create Tiny, Self-Propelled Devices"; PhysOrg.com; printed on Feb. 12, 2007; pp. 1-3; located at: http://www.physorg.com/printnews.php?newsid=90521279.

Roh et al.; "Strategy for Navigation Inside Pipelines With Differential-Driveinpipe Robot"; IEEE Xplore; 2002 and 2005; pp. 2575-2580 (Only the Abstract is being provided); vol. 3; IEEE; located at: http://ieeexplore.ieee.org/xpls/abs_all.jsp?arnumber=1013619; printed on Apr. 23, 2007.

Roh et al.; "Actively Steerable In-Pipe Inspection Robots for Underground Urban Gas Pipelines"; IEEE Xplore; bearing dates of 2001 and 2005; pp. 761-766 (Only the Abstract is being provided); vol. 1; IEEE; located at: http://ieeexplore.ieee.org/xpls/abs_all.jsp?arnumber=932642; printed on Apr. 23, 2007.

Rolfe, Brigitte; "Toward Nanometer-Scale Sensing Systems: Natural and Artificial Noses as Models for Ultra-Small, Ultra-Dense Sensing Systems"; Advances in Computers; bearing dates of Nov. 2004, 2004, and 2007; pp. 11-46; vol. 71; Elsevier, B.V.

Schertler et al.; "Effects of ECG Gating and Postprocessing Techniques on 3D MDCT of the Bronchial Tree"; AJR; bearing a date of Jul. 2004; pp. 83-89; vol. 183; American Roentgen Ray Society.

Schnakenberg et al.; "Intravascular pressure monitoring system"; Sensors and Actuators A: Physical; bearing a date of 2004; pp. 61-67; vol. 110; Elsevier B.V.

Schwartz, John; "In the Lab: Robots That Slink and Squirm"; The New York Times: Science; bearing a date of Mar. 27, 2007; pp. 1-4; The New York Times Company; located at: http://www.nytimes.com/2007/03/27/science/27robo.html?ex=1332648000&en=d4541141c174b454&ei=5124&partner=digg&exprod=digg; printed on Mar. 27, 2007.

"Spider pill to seek out diseases"; PhysOrg.com; bearing a date of Oct. 16, 2009 and 2009; p. 1; located at http://www.physorg.com/news174893082.html.

Sun et al.; "A Miniature RF Communication System for Micro Gastrointestinal Robots"; Journal of Medical Engineering & Technology; bearing a date of 2003; pp. 160-163; vol. 27.

Suzumori et al.; "Micro Inspection Robot for 1-in Pipes"; IEEE/ASME Transactions on Mechatronics; bearing dates of Sep. 1999 and 1999; pp. 286-292; vol. 4, No. 3; IEEE.

Tang et al.; "Cerebral Vascular Tree Matching of 3D-RA Data Based on Tree Edit Distance"; Medical Imaging and Augmented Reality; bearing a date of 2006; pp. 116-123.

The Biomedical Engineering Handbook, Second Edition; bearing a date of 2000; pp. IV-1—43-31; vol. I; CRC Press LLC.

The Biomedical Engineering Handbook, Second Edition; bearing a date of 2000; pp. V-1—51-9; vol. I; CRC Press LLC.

Thrun, Sebastian; "Learning Metric-Topological Maps for Indoor Mobile Robot Navigation"; Artificial Intelligence; bearing a date of 1998; pp. 21-71; vol. 99; Elsevier Science B.V.

Thrun, Sebastian; "Probabilistic Algorithms in Robotics"; AI Magazine; bearing dates of Winter 2000 and 2000; pp. 93-109; vol. 21, No. 4; American Association for Artificial Intelligence.

Thrun, Sebastian; "Robotic Mapping: A Survey"; Exploring Artificial Intelligence in the New Millenium; bearing a date of Feb. 2002; pp. 1-29 (31 total pages); Morgan Kaufmann.

Thrun et al.; "A Real-Time Algorithm for Mobile Robot Mapping With Applications to Multi-Robot and 3D Mapping"; IEEE International Conference on Robotics and Automation; bearing a date of Apr. 2000; pp. 1-8.

Tomatis et al.; "Simultaneous Localization and Map Building: A Global Topological Model with Local Metric Maps"; Robotics Autonomous Systems; bearing a date of 2003; pp. 1-6; vol. 44.

Tsuruta et al.; "Control Circuit in an In-Pipe Wireless Micro Inspection Robot"; IEEE Xplore; bearing dates of 2000 and 2005; pp. 59-64 (Only the Abstract is being provided); IEEE; located at: http://ieeexplore.ieee.org/xpls/abs_all.jsp?arnumber=903290; printed on Apr. 23, 2007.

Ulrich et al.; "Appearance-Based Place Recognition for Topological Localization"; IEEE International Conference on Robotics and Automation; bearing a date of Apr. 2000; pp. 1023-1029.

Verheye et al.; "Selective Clearance of Macrophages in Atherosclerotic Plaques by Autophagy"; Journal of the American College of Cardiology; bearing dates of Feb. 13, 2007 and 2007; pp. 706-715; vol. 49, No. 6; Elsevier Inc.

Wacharasindhu et al.; "Radioisotope microbattery based on liquid semiconductor"; Applied Physics Letters; bearing dates of Dec. 11, 2008, Jun. 9, 2009, Jul. 6, 2009, Dec. 8, 2009 and 2009; pp. 014103-1 -014103-3; vol. 95; American Institute of Physics.

Wakimoto et al.; "A Micro Snake-Like Robot for Small Pipe Inspection"; International Symposium on Micromechatronics and Human Science; bearing a date of 2003; pp. 303-308; IEEE.

Wang et al.; "A MEMS-based Air Flow Sensor with a Free-standing Micro-cantilever Structure"; Sensors; bearing dates of Aug. 27, 2007, Oct. 10, 2007, Oct. 17, 2007, and 2007; pp. 2389-2401; vol. 7; MDPI.

Watson et al.; "Piezoelectric ultrasonic resonant motor with stator diameter less than 250 µm: the *Proteus* motor"; Journal of Micromechanics and Microengineering; bearing dates of Sep. 25, 2008, Nov. 18, 2008, Jan. 20, 2009, and 2009; pp. 1-5; vol. 19; IOP Publishing Ltd.

Weingandt et al.; "Autofluorescence spectroscopy for the diagnosis of cervical intraepithelial neoplasia"; BJOG: an International Journal of Obstetrics and Gynaecology; bearing dates of Aug. 2002 and 2002; pp. 947-951; vol. 109; RCOG.

Xi et al.; "Self-assembled microdevices driven by muscle"; Nature Materials; bearing dates of Feb. 2005 and 2005; pp. 180-184 (10 pages total); vol. 4; Nature Publishing Group.

Yang et al.; "Power generation with laterally packaged piezoelectric fine wires"; Nature Nanotechnology; bearing dates of Nov. 9, 2008, Jan. 2009, and 2009; pp. 34-39; vol. 4; Macmillan Publishers Limited.

Yang et al.; "Converting Biomechanical Energy into Electricity by a MuscleMovement-Driven Nanogenerator"; Nano Letters; bearing dates of Dec. 25, 2008, Jan. 31, 2009, and 2009; pp. 1201-1205; vol. 9, No. 3; American Chemical Society.

Yu et al.; "System for the analysis and visualization of large 3D anatomical trees"; Computers in Biology and Medicine; bearing dates of Oct. 6, 2006, May 31, 2007, Jun. 4, 2007, and 2007; pp. 1802-1820; vol. 37; Elsevier Ltd.

Zhao et al.; "Physicist Develops Natural Motor Technique"; PhysOrg.com; bearing dates of Apr. 21, 2007 and 2007; 1 page; United Press International; located at: http://www.physorg.com/news96357975.html; printed on Apr. 23, 2007.

Zheng et al.; "Design and Fabrication of a Micro Coulter Counter with Thin Film Electronics"; Proceedings of 2006 International Conference on Microtechnologies in Medicine and Biology; bearing dates of May 9-12, 2006 and 2006; pp. 16-19; IEEE.

Zhu et al.; "Flattening Maps for the Visualization of Multibranched Vessels"; IEEE Transactions on Medical Imaging; bearing dates of Feb. 10, 2004, Sep. 27, 2004, Feb. 2005, and 2005; pp. 191-198; vol. 24, No. 2; IEEE.

Zrimec et al.; "3D Modelling and Visualization of the Human Lung"; Proceedings of the 2nd International Symposium on 3D Data Processing, Visualization, and Transmission (3DPVT'04); bearing a date of 2004; pp. 110-115; IEEE.

Zyga, Lisa; "Microswimmer Propels Itself With Near-Zero Friction"; PhysOrg.com; bearing dates of Jun. 4, 2007 and 2007; pp. 1-2; PhyOrg.com; located at: http://www.physorg.com/news100176842.html; printed on Jun. 6, 2007.

Agarwal, Abhishek K.; Atencia, Javier; Beebe, David J.; Jiang, Hongrui; "Magnetically-driven temperature-controlled microfluidic actuators"; printed on Nov. 13, 2008; pp. 1-5; located at: http://www.unl.im.dendai.ac.ip/INSS2004/INSS2004_papers/OralPresentations/C2.pdf.

Chen, Haitao; Ebner, Armin D.; Ritter, James A.; Kaminski, Michael D.; Rosengart, Axel J.; "Sequestration of Blood-Borne Magnetic Drug Carrier Particles Using Magnetizable Intravascular Stents"; Collaborative Investigators for Applied Nanotechnology in Medicine; printed on Nov. 13, 2008; pp. 1; Chicago, Illinois.

Martel, Sylvain; "Fundamentals of high-speed piezo-actuated three-legged motion for miniature robots designed for nanometer-scale operations"; printed on Nov. 13, 2008; pp. 1-8.

* cited by examiner

CILIATED STENT-LIKE-SYSTEM

CROSS-REFERENCE TO RELATED APPLICATIONS

The present application is related to, claims the earliest available effective filing date(s) from (e.g., claims earliest available priority dates for other than provisional patent applications; claims benefits under 35 USC §119(e) for provisional patent applications), and incorporates by reference in its entirety all subject matter of the following listed applications; the present application also claims the earliest available effective filing date(s) from, and also incorporates by reference in its entirety all subject matter of any and all parent, grandparent, great-grandparent, etc. applications of the following listed applications:

1. United States patent application entitled A SYSTEM FOR PERFUSION MANAGEMENT, naming Lowell L. Wood Jr. as inventor, filed 19 Apr. 2004 and assigned U.S. application Ser. No. 10/827,576.
2. United States patent application entitled A SYSTEM WITH A SENSOR FOR PERFUSION MANAGEMENT, naming Lowell L. Wood Jr. as inventor, filed 19 Apr. 2004 and assigned U.S. application Ser. No. 10/827,578.
3. United States patent application entitled A SYSTEM WITH A RESERVOIR FOR PERFUSION MANAGEMENT, naming Lowell L. Wood Jr. as inventor, filed 19 Apr. 2004 and assigned U.S. application Ser. No. 10/827,572.
4. United States patent application entitled A TELESCOPING PERFUSION MANAGEMENT SYSTEM, naming Lowell L. Wood Jr. as inventor, filed 19 Apr. 2004 and assigned U.S. application Ser. No. 10/827,390.

TECHNICAL FIELD

The present application relates, in general, to endoprosthetic devices for the treatment and/or management of disease, disorders, or conditions.

SUMMARY

In one aspect, a device includes but is not limited to: a flexible hollow portion with an outer surface and an inner surface and wherein the flexible hollow portion is sized for placement in a location in a receiver; and a plurality of movable parts coupled to the inner surface of the flexible hollow portion, the movable parts operable as a group for moving particles. In addition to the foregoing, other method aspects are described in the claims, drawings, and text forming a part of the present application.

In one aspect, a method includes but is not limited to: forming a supporting passage implantable in an animal; coupling a plurality of moving parts to the supporting passage; and sizing the supporting passage and the plurality of moving parts coupled to the supporting passage for placement in a location in the animal. In addition to the foregoing, other method aspects are described in the claims, drawings, and text forming a part of the present application.

In one aspect, a method includes but is not limited to: placing a hollow expandable device in a luminal portion of a recipient wherein the interior of the hollow expandable device is coupled to a plurality of moving pieces; positioning the hollow expandable device in the lumen of the organ; and monitoring the hollow expandable device. In addition to the foregoing, other method aspects are described in the claims, drawings, and text forming a part of the present application.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one or more various aspects, related systems include but are not limited to energy- and power-management circuitry and/or programming for effecting the herein-referenced method aspects; the circuitry and/or programming can be virtually any combination of hardware, software, and/or firmware configured to effect the herein-referenced method aspects depending upon the design choices of the system designer.

In addition to the foregoing, various other method and or system aspects are set forth and described in the text (e.g., claims and/or detailed description) and/or drawings of the present application.

The foregoing is a summary and thus contains, by necessity; simplifications, generalizations and omissions of detail; consequently, those skilled in the art will appreciate that the summary is illustrative only and is NOT intended to be in any way limiting. Other aspects, inventive features, and advantages of the devices and/or processes described herein, as defined solely by the claims, will become apparent in the non-limiting detailed description set forth herein.

BRIEF DESCRIPTION OF THE FIGURES

The use of the same symbols in different drawings typically indicates similar or identical items.

DETAILED DESCRIPTION

The present application uses formal outline headings for clarity of presentation. However, it is to be understood that the outline headings are for presentation purposes, and that different types of subject matter may be discussed throughout the application (e.g., device(s)/structure(s) may be described under the process(es)/operations heading(s) and/or process(es)/operations may be discussed under structure(s)/process(es) headings). Hence, the use of the formal outline headings is not intended to be in any way limiting.

1. A Ciliated Stent-Like System(s) and/or Process(es).

Figure 1:
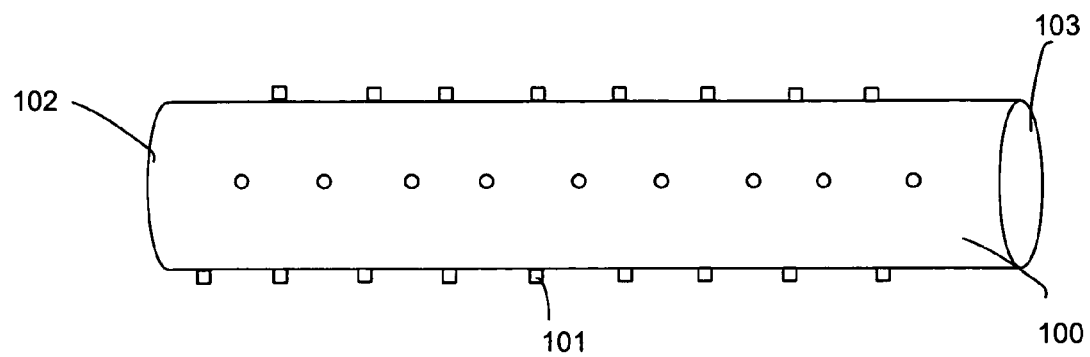
FIG. 1 is a plan view of an embodiment of ciliated stent-like system 100.

With reference now to FIG. 1, shown is a side plan view illustrative of various exemplary ciliated stent-like system(s) and/or process(es). Accordingly, the present application first describes certain specific exemplary structures of FIG. 1; thereafter, the present application illustrates certain specific exemplary processes. Those having skill in the art will appreciate that the specific devices, systems and processes described herein are intended as merely illustrative of their more general counterparts.

It will also be appreciated by those skilled in the art that in one embodiment, the ciliated stent-like system includes a powered ciliated stent-like system. Furthermore, while the structure is referred to as a ciliated stent-like system, the terminology is not intended to be limiting. The term stent-like system may for example, refer stents or similar devices that may include any structure or device for providing support to an orifice, such as, for example, slender rods, threads, or catheters.

A. Structure(s) and or Device(s)

With reference to the figures, and with reference now to FIG. 1, shown is a plan view of a ciliated stent-like system 100. The ciliated stent-like system 100 is an endoprosthetic device which may be employed in a recipient, a receiver, or a host, for example, an animal. In one aspect, the ciliated stent-like system 100 may be inserted into a lumen of a vessel threading a tissue or organ or portion thereof. The surface of the ciliated stent-like system 100 may include surface modifications to attach to or to positionally contact the vessel walls of the animal. For example, the surface modifications may include bumps 101, rings, grooves, ridges, or contours, one or more of which may be power-actuated. In one aspect, the ciliated stent-like system 100 is a longitudinal or elongated device with a substantially hollow interior. The ciliated stent-like system 100 may be used as an intraluminal prosthetic device to repair, open, evacuate, replace, medicate or support a lumen in the recipient. For example, the lumen of a vessel threading a tissue or an organ may be a part of a vascular system, a neurovascular system, a urogenital tract, a pulmonary tract, a gastrointestinal tract, or any other lumen-threaded tissue or organ or portion thereof.

Figure 2:
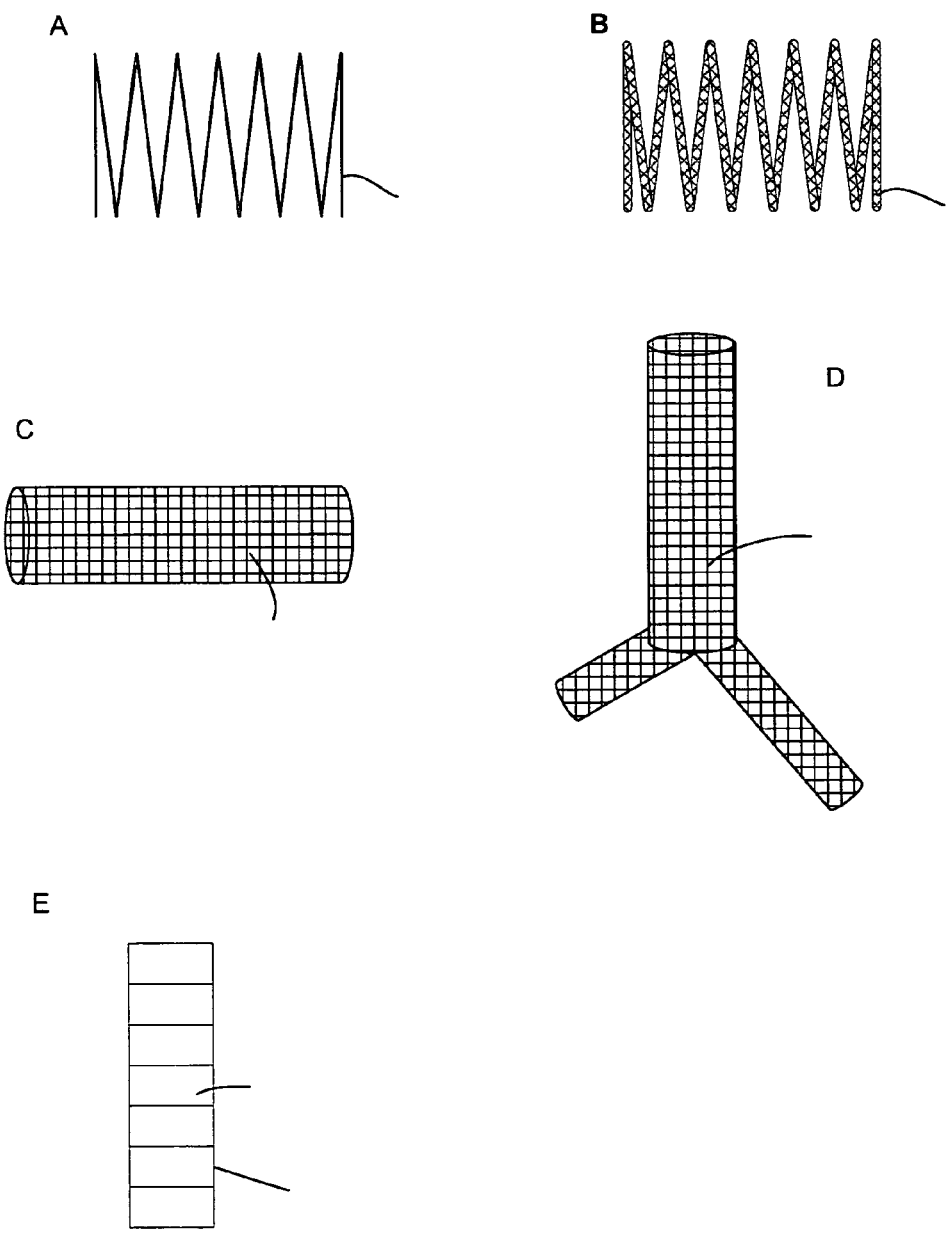
FIG. 2 is a plan view of various aspects of the ciliated stent-like system 100.

With reference to the figures, and with reference now to FIG. 2, depicted is a plan view of various aspects of the ciliated stent-like system 100. In one aspect, the ciliated stent-like system 100 may have an open configuration. In another aspect, the ciliated stent-like system 100 may have a flexible, compressible, or expansive configuration. The ciliated stent-like system 100 may be self-expanding, balloon expandable, dilatable or contractible under control of an embedded controller. Expansion may be achieved, for example, by including an expandable material or a specific configuration, or a combination. For example, the expandable material, includes but is not limited to, nickel-cobalt-chromium based alloys, or titanium. Furthermore, expandability can also be configured by using a coil or spring-like configuration, or via any of many types of powered devices or mechanisms.

Continuing to refer to FIG. 2, in another aspect, the ciliated stent-like system 100 may have an open flexible configuration. Such a configuration would permit the ciliated stent-like system 100 to be minimized in size for insertion. On insertion at a location the ciliated stent-like system 100 may expand to provide support. The shape or type of the ciliated stent-like system 100 may depend on the location of its use. For example, the ciliated stent-like system 100 may have a helical coil shape (FIGS. 2A and 2B), a tubular mesh shape (FIG. 2C), a bifurcated shape (FIG. 2D), an irregular Y shape, or an elongated segmented shape including taper (FIG. 2E). In one aspect, the ciliated stent-like system 100 may be formed from a single wire, or have an open lattice or network structure. Additional information can be found, for example, in U.S. Pat. Nos. 5,395,390 and 5,234,457 both of which are hereby incorporated by reference in their entirety. In one aspect, the ciliated stent-like system 100 may include a segmented structure, for example, for promoting flexibility and closer adherence to the lumen. In another aspect, the ciliated stent-like system 100 may include one or more expandable forks or branches, for example, for enhancing the support and/or removal of occluded material. Additionally, the ciliated stent-like system 100 may include attachments, including but not limited to, an evacuating device, a siphon, a sensor, an actuator, a device for storing materials, a device for releasing materials stored, a controller, or a device for providing telemetry solutions.

Some or all of the parts, for example, the tissue-contacting parts, of the ciliated stent-like system 100 may be formed from a biocompatible material, a shape memory material or a metal such as, for example, nickel titanium alloy, metal, silicon, plastic or polymer. Examples of polymers include but are not limited to, polyethylene, polypropylene, polyglycolic acid, polylactic acid, cellulose acetate, or cellulose nitrate. In one aspect some or all of the parts of the ciliated stent-like system 100 may be made of a biodegradable material. In another aspect, the ciliated stent-like system 100 may be coated by one or more polymers or materials which are, for example, biocompatible, organic or biodegradable.

Furthermore, the ciliated stent-like system 100 may be used to deliver an agent, for example, including but not limited to, by passive delivery or under control of an controller either internal or external to the ciliated stent-like system 100. In one aspect, when delivering the agent by passive delivery, the ciliated stent-like system 100 may be coated with one or more agents, such as, for example, including, but not limited to, a drug, a medicinal agent, a therapeutic agent, a biologically active agent, a chemical, a chemical compound, a surfactant, a steroid, a luminal-dilating agent, a luminal-contracting agent, an antibiotic or antifungal or antiviral agent, a protein, a nucleic acid or a polymer comprised of one or more nucleic acids, a macromolecule, or a peptide.

In one aspect the ciliated stent-like system 100 is sized for placement in the recipient, for example, including but not limited to, in a lumen of a blood vessel in an adult human body. In another aspect the ciliated stent-like system 100 is sized for placement, for example, in the lumen of an organ in a pediatric body. In one example, the size of the diameter of the stent may be about 1-2 cm. In another example, both of the exterior and the interior diameters of the ciliated stent-like system 100 may be uniform or may vary to accommodate dimensions of the location of insertion, placement of functionality-conferring devices, or functionality of the ciliated stent-like system 100. In another example, the ciliated stent-like system 100 may be sized to fit within a portion of a bronchial tree, wherein the internal diameter of portions of the bronchial tree is about 0.1-10 mm. It is also within the scope of the invention, that the ciliated stent-like system 100 may be used to replace, fully or partially, the functionality of the section portion of the bronchial tree. In this example, the outer diameter of the ciliated stent-like system 100 has a diameter corresponding to about the external diameter of the portion of the bronchial tree.

Figure 3:
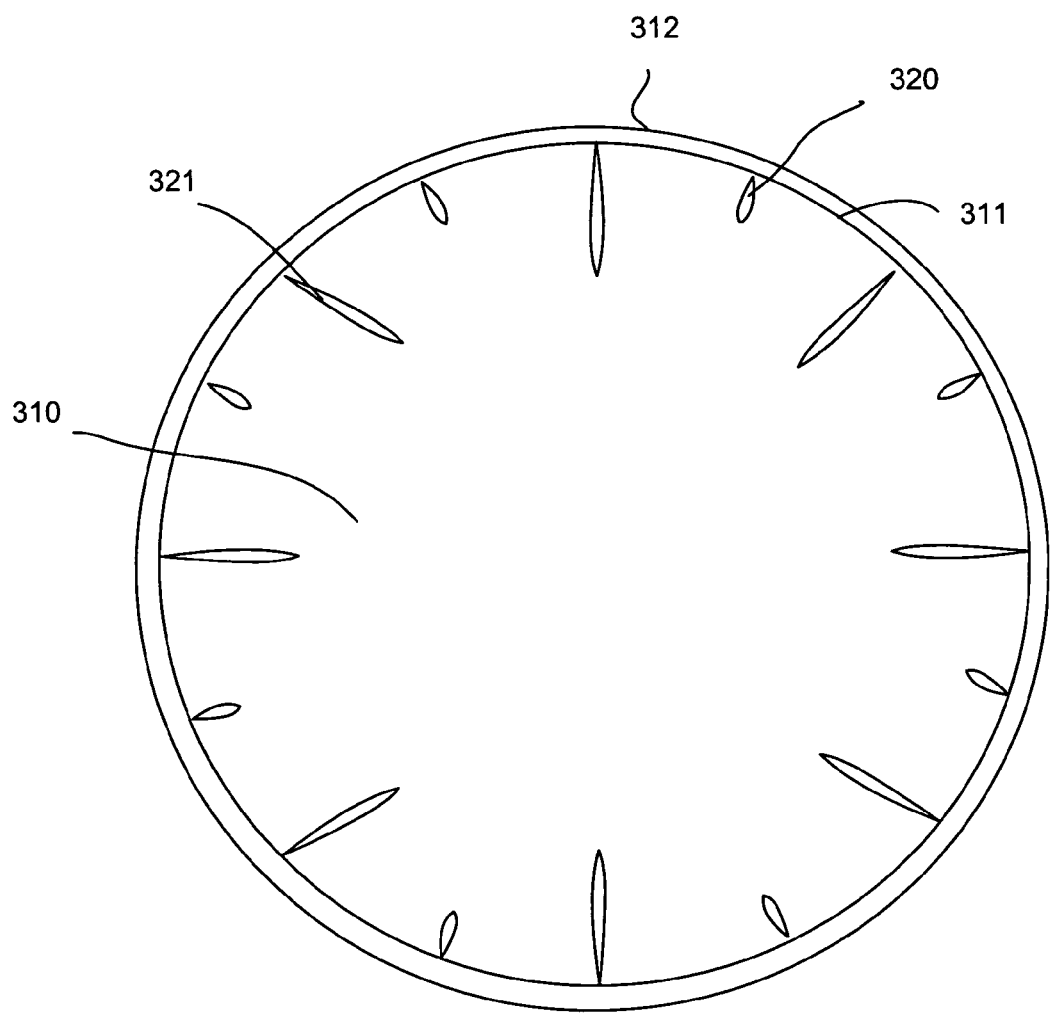
FIG. 3 is one aspect of a cross sectional view of the ciliated stent-like system 100.
Figure 4:
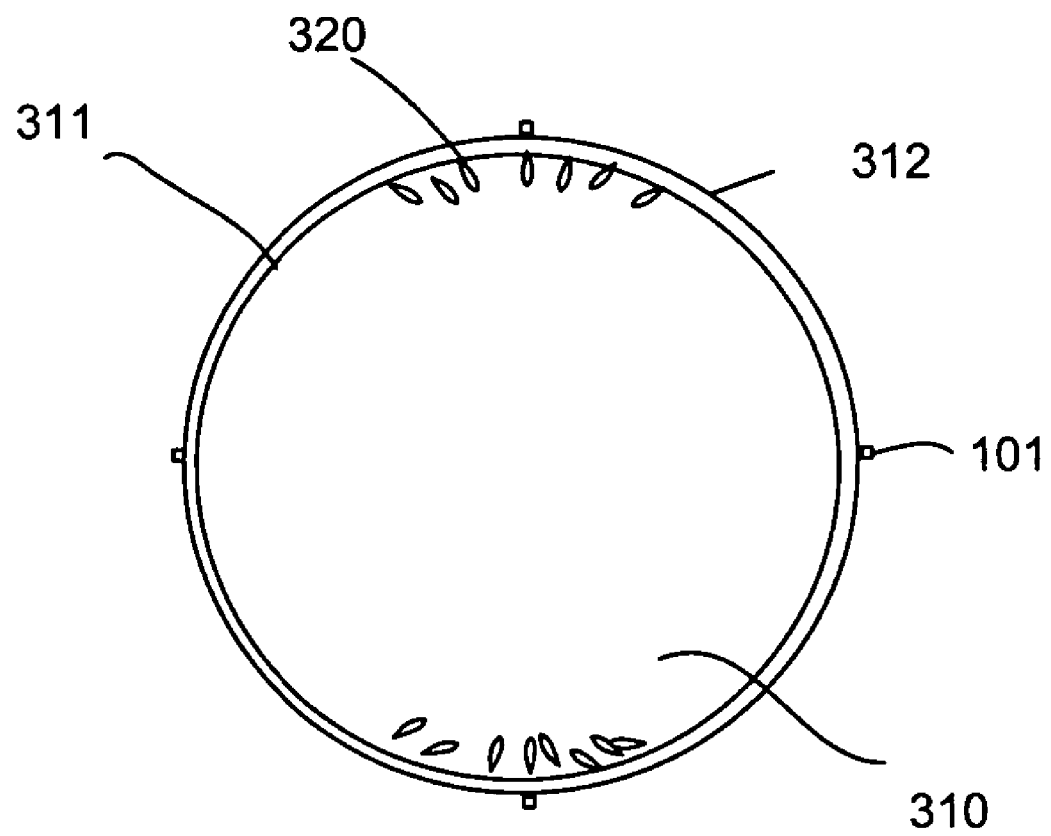
FIG. 4 is one aspect of a cross sectional view of the ciliated stent-like system 100.

With reference now to FIG. 3, and with reference now to FIG. 4, depicted is one aspect of a cross sectional view of the ciliated stent-like system 100. In one aspect, the ciliated stent-like system 100 may have an outer surface 312 made of a metal and coated with a polymer. The outer surface 312 may have a coefficient of friction lower or higher in comparison to an inner surface 311 promoting the adherence of the outer surface 312 of the ciliated stent-like system 100, for example, to the bounding walls of the lumen. The outer surface 312 may also include surface protuberances 101, for example, to position or adhere the ciliated stent-like system 100, for example, to the bounding walls of the lumen. The inner surface 311 may have a low coefficient of friction to promote flow of air, fluid, debris, fluidized particles, exudates, particles, mucus, or debris. The inner surface 311 may be smooth to decrease the attachment or adherence of materials, thereby decreasing occlusion. The overall coefficient of friction of the outer surface 312 need only be of a sufficient value to permit the device to be reasonably secured to and/or positioned within a region and to minimize unwanted migration. Thus, the value of the coefficient of friction, for the ciliated stent-like system 100, will vary and, in one example, depend on the location of its use, or its intended use. It is known in the art that the coefficient of friction of Teflon-coated surfaces, for example, is about 0.05, the coefficient of friction of skin is about 0.8, and that of steel is about 0.58. In one exemplary aspect, the coefficient of friction of the inner surface 311 is between 0.0001 to about 0.58, whereas the coefficient of friction for the outer surface 312 is at least about 0.0001. In other applications or other aspects, the coefficient of friction of the inner surface 311 and the coefficient of friction for the outer surface 312 may differ from these ranges, and the ranges should not be considered limiting.

In one aspect, the ciliated stent-like system 100 has a plurality of cilia 320 and 321 arranged in the inner surface 311 of the ciliated stent-like system 100. The plurality of cilia may include one or more movable parts attached to the ciliated stent-like system 100. In one aspect, the plurality of cilia 320 and 321 may be arranged, for example, in rows, columns, or similarly-ordered groupings. The plurality of cilia 320 and 321 may fully or partially encompass the inner surface 311. In one aspect, the length, the dimensions or other configuration aspects of the cilia will depend on the intended functions of the cilia. For example, where a pulmonary ciliated stent is employed in a trachea or a bronchi, the ciliary movement may help degrade occlusions or the formation thereof. In this example, the cilia may be long, the undulatory movement of the cilia may be responsible for moving, expelling or propelling, for example, fluid, clots, occlusive material, or fluid, particles, fluidized particles, mucus, exudate or biological debris. In another aspect, the plurality of cilia 320 and 321, may be a combination of various ciliary lengths suitable for operating an undulating propelling mechanism. It will be appreciated by those skilled in the art that the plurality of cilia 320 and 321 includes, but is not limited to, cilia-like functional structures and/or cilia-like appearing structures.

In one aspect the plurality of cilia 320 and 321 may be arranged on the inner surface 311 of the ciliated stent-like system 100. However, it is within the scope of the invention to include the plurality of cilia 320 and 321 on the outer surface 312 or on both surfaces. It is also within the scope of the invention, that the plurality of cilia 320 and 321 present on the outer surface 312 or the inner surface 311 may differ, for example, in the type of cilia, control mechanism associated with the cilia, and/or the function performed by the plurality of cilia 320 and 321. For example, the plurality of cilia 320 and 321 present on the outer surface 311 may be of a type, or have features that aid in the placement of the ciliated stent-like system 100 in a location in a recipient whereas the plurality of cilia 320 and 321 present on the inner surface 312 may be of a type or have features that perform other functions.

Figure 5:
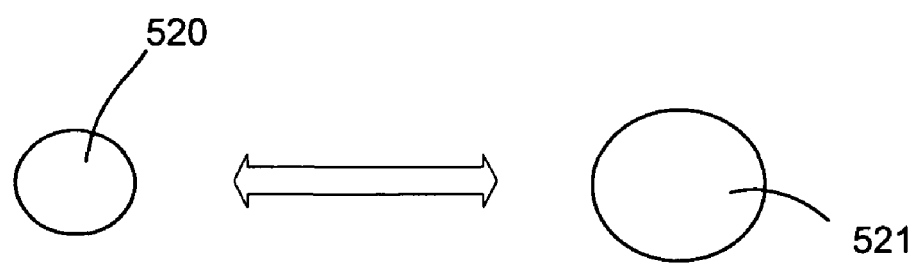
FIG. 5 is a diagrammatic view of one aspect of the ciliary movement in the interior of the ciliated stent-like system 100.
Figure 5:
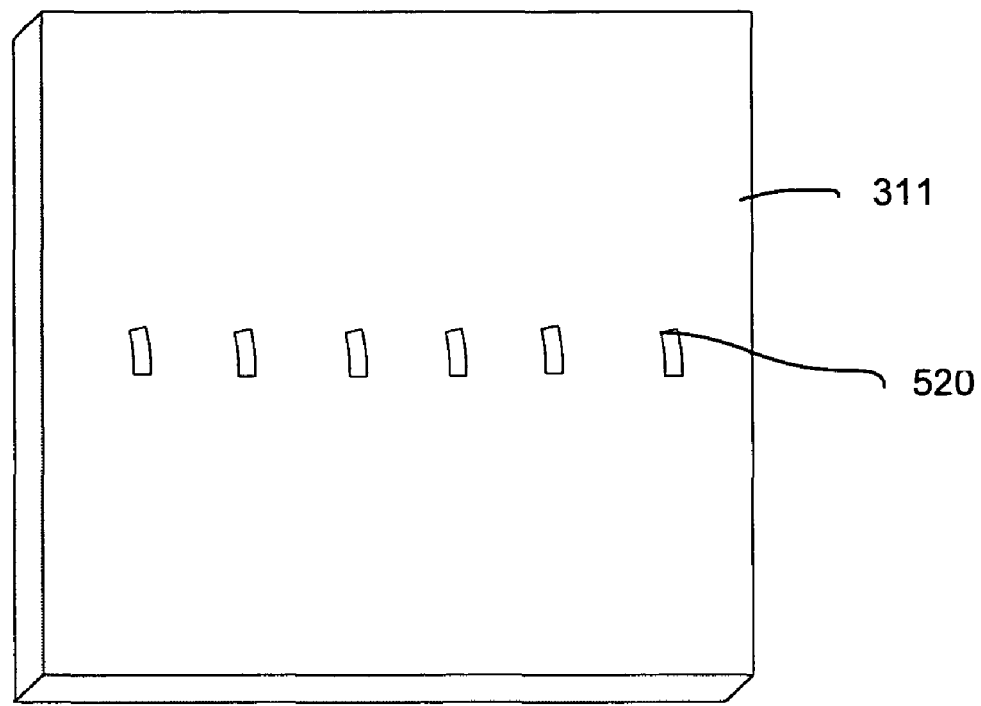

With reference now to FIG. 5, in one aspect, the plurality of cilia 320 and 321 may include an actuator made of a self-oscillating polymer gel. Additional information may be found in an article by O. Tabata, H. Hirasawa, K, and S. Aoki "Ciliary Motion Actuator using Self-Oscillating gel." The 14th Annual International Conference On Micro ElectroMechinical Systems, pp. 405-408, 2001, which is herein incorporated by reference. In another aspect, both the plurality of cilia 320 and 321 may be made of self-oscillating polymer gel. The self-oscillating polymer gel exhibits spontaneous swelling 520 and deswelling 521 and is responsible for propagating a wave motion. Ciliary movement, includes but is not limited to, up and down, undulating, wave like, pulsing, vectorial, oscillating, circular, lateral, vertical, rhythmic, or sideways movement or the like. Ciliary movement need not be limited to larger movements, but may include nanoscale-level movements.

Ciliary movement may be self-propagating or induced. For example, with regards to a pulmonary ciliated stent, induction may occur when a particle touches a cilium, or when the patient coughs, or otherwise moves or actuates his/her chest. Actuation may make use of stored energy, derived, for example, from previous motion; in the pulmonary case, for example, this motion may be that associated with inhalation and/or exhalation or with myocardial motion. The ciliated stent-like system 100 may be part of a disposable stent, for example, where the majority of the stent is composed of biodegradable or other material subject to solubilization or disintegration within the body. It will be appreciated by those skilled in the art that techniques for fabricating such cilia from self-oscillating polymer gels are well known in and are herein incorporated by reference. It will also be appreciated by those skilled in the art that techniques for favoring ciliary-driven transport in one direction along the stent relative to the other, particularly when a power source is available, are well-known and are herein incorporated by reference.

In another aspect, the plurality of cilia 310 and 321 includes one or more flexible polymeric rods. Additional information may be found in a presentation by R. L. Carroll, B. Wilde, R. M. Taylor, L. Vicci, S. Washburn, and R. Superfine, "Biomimetic Flexible Polymer Rods—Artificial Cilia." The 70th Annual meeting of the Southeastern Section of the American Physical Society, Nov. 6-8, 2003. Polymeric rods imitating ciliary structures are known structures. The polymeric rods may have a length about 10 microns, and a diameter of about 800 nm and would be able to propel fluid, fluidized particles, mucus, exudate or biological debris. However, polymeric rods of different dimensions are within the scope of the invention. In one example, the one or more flexible polymeric rods includes magnetic material. External oscillating magnetic fields may manipulate or actuate the flexible polymeric fields, for example, directly or by inductive coupling to an energy-store and/or power supply within the stent. It will be appreciated by those skilled in the art that such techniques and similar techniques are known, and are herein incorporated by reference.

In another aspect, the plurality of cilia 320 and 321 includes one or more MEMS micro-actuator arrays. It will be appreciated by those skilled in the art that the one or more MEMS micro-actuator arrays may be made to perform various modes of oscillatory movement and could be included in the interior of the ciliated stent-like system 100, for example, to provide a force for moving fluid, particles, fluidized particles, mucus, exudate or biological debris through the interior of the ciliated stent-like system 100. It will be appreciated by those skilled in the art that MEMS fabrication and actuation techniques are known in the art, and are herein incorporated by reference.

Figure 6:
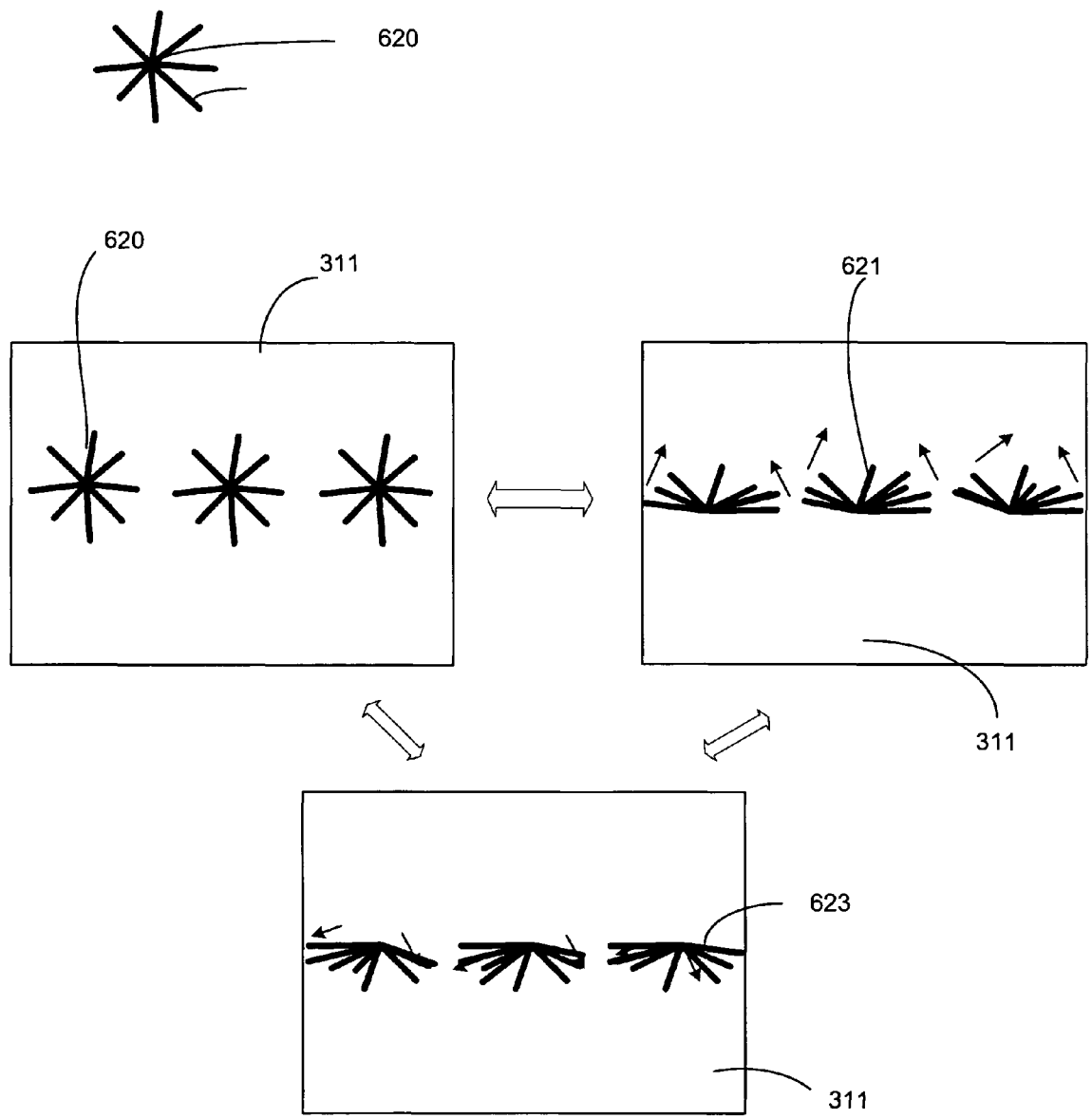
FIG. 6 is a diagrammatic view of one aspect of the ciliary movement in the interior of the ciliated stent-like system 100.

With reference now to the FIG. 6, in one aspect, the plurality of cilia 320 and 321 are arranged, for example, in a centralized group or an array 620. Each cilium may have, for example, a modified paddle-shaped structure for efficiently moving fluid, fluidized particles, particles, mucus, exudate or biological debris.

In one aspect, the plurality of cilia 310 and 321 or the array 620 includes one or more actuator arrays, for example, MEMS actuator arrays. The MEMS actuator arrays may be coated with a thin film of a material that improves the physical, chemical, or electronic, properties of the array, for example, including, but not limited to, polyimide. The MEMS actuator arrays may promote the sensorless manipulation of small objects using thermal and electrostatic control mechanisms. In one aspect the MEMS actuator arrays may be arranged, for example, including but not limited to, on the inner surface 311 of the ciliated stent-like system 100. The actuator arrays may be capable of providing a wide variety of movements, such as, for example, translation, rotation, centering, or orientation. Additionally, they may induce a low-level gait to the plurality of cilia 320 and 321, such as, for example, up-and-down motion, cyclical motion, or flagelatory motion resulting in the fluid, particles, fluidized particles, mucus, exudate or biological debris, being moved. In this example, the speed of the moving fluid, particles, fluidized particles, mucus, exudate or biological debris is dependant on the displacement of the actuators per cycle, the number of times the cycle is repeated per unit of time, the surface properties of the particle to be moved, the weight of the particle to be moved, the local surface tension, the local orientation relative to the direction of gravity or other acceleration field, etc. In another example, the one or more MEMS actuator arrays may be used to induce a high-level control, or a high-level gait, such as, for example, orienting and aligning fluid, particles, fluidized particles, mucus, exudate or biological debris. In this example, the one or more MEMS actuator arrays may be used to position or rotate an obstructing or blocking particle for its expulsion or removal from the lumen of a vessel. It will be appreciated by those skilled in the art that such techniques are known in the art and are herein incorporated by reference. Additional information may be found in an article by W. Suh, R. B. Darling, K. F. Böhringer, B. R. Donald, H. Baltes, G. T. A. Kovacs, "Fully Programmable MEMS Ciliary Actuator Arrays for Micromanipulation Tasks." IEEE International Conference on Robotics and Automation (ICRA), pp. 1101-1108, San Francisco, Calif., April 2000, which is herein incorporated by reference.

Continuing to refer to FIG. 6, in one example, the plurality of cilia 320 and 321, for example, may move in a programmed or otherwise controlled rhythm. The plurality of cilia 320 and 321 may extend to an upward extended position 621 from a middle resting position, to a downward position 623 before returning to the middle resting position. In another example the resting position of the plurality of cilia 320 and 321 may be the downward position 623. Other combinations of synchronous or non-synchronous beatings of the plurality of cilia 320 and 321 are within the scope of the invention, including those in which one or more waves of ciliary action are made to propagate along some selected direction relative to the local axis of the stent.

In another aspect, motors may be included in the plurality of cilia 320 and 321 to provide the energy or to generate the force needed for moving fluid, particles, fluidized particles, mucus, exudate or biological debris or fluid. In one example, protein molecule-based motors, such as those employing kinesin or dynein, may be used to provide motive force for ciliary rotational or directional movement. For example, including but not limited to, the direction of the movement of the biological molecular motors, is influenced by the orientation of any tubulin present, or the matrix that the motors may use as their tracks. In one aspect, ATP hydrolysis may provide the energy for the actuation of the biological molecular motors, and ATP and ATPase may be furnished, for example, by coupling mitochondria to the biological molecular motors. In another example, the actin-myosin system may be included in the plurality of cilia 320 and 321 in order to provide the force for moving fluid, particles, fluidized particles, mucus, exudate or biological debris. It will be appreciated by those skilled in the art that such techniques are known in the art and are herein incorporated by reference. This subject is described in further detail by N. Thomas and R. A. Thornhill in the Journal of Physics D: Applied Physics 31, pages 253-266, 7 Feb. 1998, and by Carlo Montemagno, George Bachand, Scott Stelick, and Marlene Bachand in Nanotechnology 10:225-231, 1999, both of which are herein incorporated by reference.

In another aspect, the plurality of cilia 320 and 321 includes an electro-active transducer with an electroactive polymer, which deflects in response to an electrical field. In one example, the deflection of the electroactive polymer is operable to move fluid. In another example, the deflection of the electroactive polymer is operable to move fluid, particles, fluidized particles, mucus, exudate or biological debris, such as, for example, congealed or clotted liquids. The transducer includes at least two electrodes in electrical communication with the electroactive polymer. Deflection of the electroactive polymer may produce a range of motions, including, but not limited to, one or more of a rotational, vibrational, linear, flagelatory or the like. Additional information regarding electroactive polymers can be found in U.S. Patent Application No. 2004/0008853 which is herein incorporated by reference.

In another aspect, the plurality of cilia 320 and 321 includes, for example, electrostrictive materials, such as, piezoelectric materials, or magnetostrictive materials. These materials may be actuated by application of electric or magnetic fields, respectively, sourced, for example, by a power source internal or external to the ciliated stent-like system 100. In one aspect, the power source may be external to the ciliated stent-like system 100 but internal to the recipient. For example, including, but not limited to, acoustic energy may be sourced from either within the ciliated stent-like system 100, from elsewhere within the recipient in which the ciliated stent-like system 100 is located. In another aspect, the power source may be external to the recipient, for example, power may be supplied to the ciliated stent-like system 100 from outside of the recipient, including powering actuation of the plurality of cilia 320 and 321, either directly or indirectly. In yet another aspect, the power source may be internal to the ciliated stent-like system 100.

In another aspect, control of ciliary motion may be performed by a controller, for example, including, but not limited to, one centered on a digital microprocessor, embedded in whole or in part within the ciliated stent-like system 100 or the powered stent-like system. Such embedded controller may be interrogated or programmed with acoustic-, wired- or optical-circuitry or via wireless transmission of electrically-, magnetically- or electromagnetically-conveyed signals. Such controller may be informed by one or more sensors within the ciliated stent-like system 100 or the powered stent-like system. Such controller may, from time-to-time in a programmed manner, also direct release of one or more materials from one or more reservoirs or storage compartments located within the ciliated stent-like system 100 or the powered stent-like system, or may direct, monitor or control one or more large-scale motions of part or all of the ciliated stent-like system 100 or the powered stent-like system system 100.

Provision of energy to the power the ciliated stent-like system 100 includes, but is not limited to, including one or more primary or secondary batteries possibly embedded into, battery-recharging or direct power transfer via body-external magnetic, electric, acoustic, gross-mechanical-motion or optical fields applied for this purpose, a system generating chemical energy possibly embedded within the system. In one aspect, energy may be recharged or regenerated. For example, by external or intra-body sources, and transduction/ conversion of kinetic energy deriving from action of one or more muscles of the body in which the ciliated stent-like system 100 or the powered stent-like system is embedded or implanted, for example, including but not limited to, inertial-mechanical-electrical transduction.

The ciliated stent-like system 100 or the powered stent-like system may include additional devices, integrated devices, or properties for diametrically expanding and/or contracting, as well as translating along the axis of the local lumen, any portion of the system, including all of it. These may include, but aren't limited to, mechanical devices, such as, for example, linear motors, electro- or magneto-strictive actuators, tractive devices, pneumatic actuators, peristaltic devices, etc.

The ciliated stent-like system 100 or the powered stent-like may include additional devices, integrated devices, or properties for sensing and/or quantitatively measuring to a specified accuracy one or more features or variables of its environment, for processing, storing and transmitting such information to a body-external receiver, and for receiving control or interrogation information from one or more body-external points.

The format of materials which may be stored and/or released by the ciliated stent-like system 100 includes, but is not limited to, liquids, gases, emulsions, gels, mists, sprays, dusts, powders, aerosolized or carbureted particulate matter of all types, and the composition thereof may be one or more of a drug, a medicinal agent, a therapeutic agent, a biologically active agent, a chemical, a chemical compound, a surfactant, a steroid, a luminal-dilating agent, a luminal-contracting agent, an antibiotic or antifungal or antiviral agent, a protein, a nucleic acid or a polymer comprised of one or more nucleic acids, a macromolecule, or a peptide, a contrast agent, or a pharmacological agent.

B. Operation(s) and/or Process(es)

Figure 7:
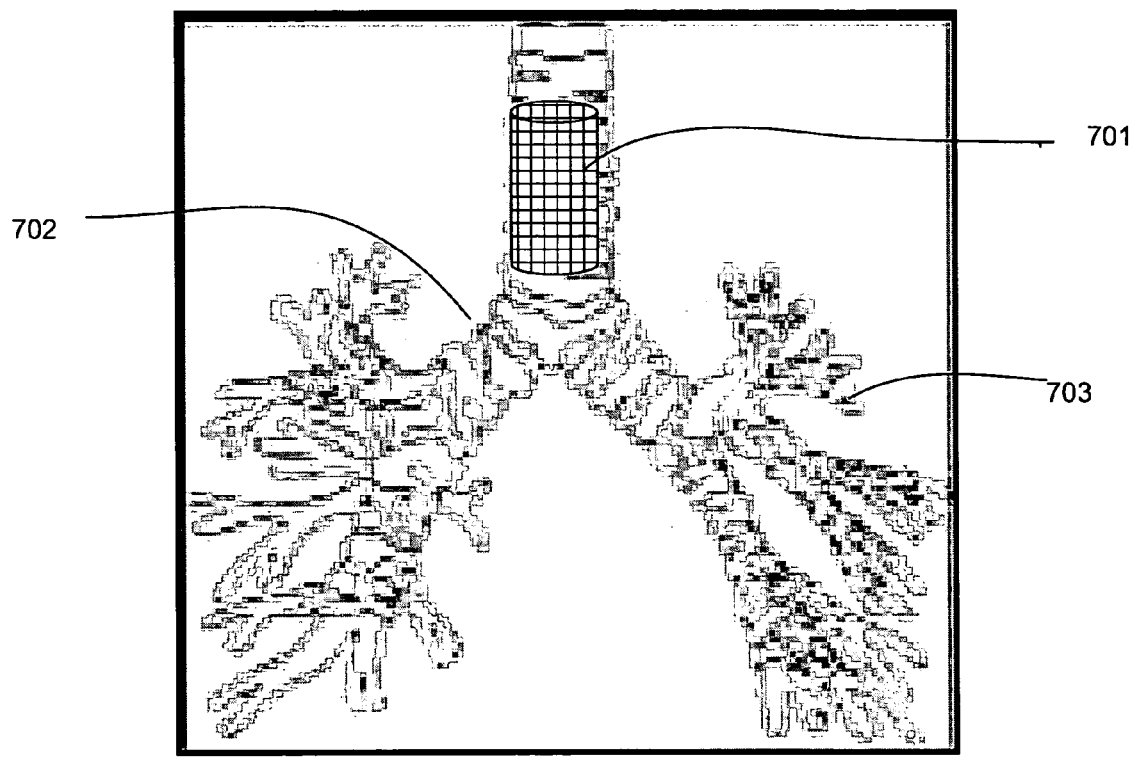
FIG. 7 is an illustration of the ciliated stent-like system 100 implanted in a trachea or a bronchial tree portion 701.

With reference to the figures, and with reference now to FIG. 7, is an illustration of the ciliated stent-like system 100 implanted in a trachea 701. In another implementation the ciliated stent-like system 100 is implanted in a bronchiole 703, or a bronchi 702 or any part of the bronchial tree. In other implementations, the ciliated stent-like system 100 is not restricted to the pulmonary system but is employed in the lumen of any vessel or organ of the recipient, for example, any vessel in an animal body.

In one implementation, the ciliated stent-like system 100 includes, but is not limited to, an external controller for manipulating the ciliated stent-like system 100 and/or the plurality of cilia 320 and 321. Manipulation of the ciliated stent-like system 100 may include, for example, expelling, moving, guiding, positioning or repositioning the ciliated stent-like system 100. In one example, the ciliated stent-like system 100 may be controlled or manipulated from a remote location by medical personnel. In another example, the ciliated stent-like system 100 may be controlled or manipulated external to the recipient. In another implementation, the external controller may include a monitoring system, and/or wireless circuitry for manipulating the ciliated stent-like system 100 0 and/or the plurality of cilia 320 and 321.

In one implementation, the ciliated stent-like system 100 includes a system or apparatus for removing or relocating biological debris of various types, such as, for example, fluid, particles, fluidized particles, mucus, exudate or biological debris. For example, the apparatus or the system may include a siphon connected to a monitor for visualizing the debris field. Observable debris may then be siphoned by positioning and operating the siphon. In one example, the siphon may be used in collaboration with the plurality of cilia 320 and 321. In this example, the plurality of cilia 320 and 321 may be used to gather and/or expel any debris and the siphon employed to collect and/or relocate the gathered or expelled debris, for example, from within one or more locations in the pulmonary tract into the esophagus.

In one implementation, the use of the ciliated stent-like system 100 includes, but is not limited to, the treatment of pulmonary diseases, such as, for example, chronic obstructive pulmonary disease (COPD). COPD includes diseases characterized by dyspnea or disorders characterized by, such as, for example, chronic bronchitis, asthma, or emphysema. Additional information may be found in the following two articles by P. J. Barnes, "Small Airways in COPD," New England Journal of Medicine, 350:256, pages 2635-2637, Jul. 04, 2004, and by E. R. Sutherland, R. M. Cherniack, "Management of Chronic Obstructive Pulmonary Disease", pages 2689-2697, Jun. 24, 2004, which is herein incorporated by reference. In another implantation, the ciliated stent-like system 100 may be configured to address diseases, such as, for example, cystic fibrosis, in which under-performance of the muco-ciliary system results in the accumulation of mucus, exudates and pathogens in the lung, causing prolonged, occasionally life-threatening infections. In this example, the ciliated stent-like system 100 may be employed to help clear the air passages by expelling actively, for example, fluid, fluidized particles, mucus, exudate or biological debris, including in conjunction with release and/or dispersal of surfactants or viscosity-modulating agents, either from the ciliated stent-like system 100 or from other sources.

In one implementation, the plurality of cilia 320 and 321 are programmed for moving intermittently. In another implementation, the plurality of cilia 320 and 321 may be programmed to move continuously. It will be appreciated by those skilled in the art that the movements of the plurality of cilia 320 and 321 may be adjusted depending on a number of criteria, for example, the area of use or the specifics of the task required to be performed.

C. Variation(s), and/or Implementation(s)

Those having skill in the art will recognize that the present application teaches modifications of the devices, structures, and/or processes within the spirit of the teaching herein. For example, the ciliated stent-like system 100 need not be limited to a cylindrical or tubular shape. For example, the ciliated stent-like system 100 may have a composite or multi-segmented flexible shape to provide a best fit in the use-location in the animal. In another example, the ciliated stent-like system 100 may have a substantially planar or conical shape, or may change its shape markedly as it installs within or transverses a luminal tract of a vessel within an animal. Other modifications of the subject matter herein will be appreciated by one of skill in the art in light of the teachings herein.

It will also be appreciated by those skilled in the art that the ciliated stent-like system 100 may be made of materials that render it fully or partially disposable. In one example, the outer surface 312 of the ciliated stent-like system 100 is designed to deliver an agent or perform functions to remove an obstruction, and then disintegrate. For example, the outer surface 312 of the ciliated stent-like system 100 may be coated with the agent which is made to contact the walls of the lumen. The main body of the ciliated stent-like system 100 may be designed to disintegrate or dissolve over a certain interval of time leaving the agent on/within the lumen. Alternatively, the ciliated stent-like system 100 may release one or more agents into the lumen itself, either continually or under program control. Any such agent may be replenished by reloading into a compartment or reservoir within the ciliated stent-like system 100. Other modifications of the subject matter herein will be appreciated by one of skill in the art in light of the teachings herein.

It will also be appreciated by those skilled in the art that the ciliated stent-like system 100 may include wireless or robotic attachments for controlling it from the exterior of the recipient or animal in which it is placed. Other modifications of the subject matter herein will be appreciated by one of skill in the art in light of the teachings herein.

The foregoing described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular aspects of the present subject matter described herein have been shown and described, it will be obvious to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is defined solely by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations), etc.

The invention claimed is:

1. A device, comprising:
    a flexible hollow portion with an outer surface and an inner surface;
    a plurality of movable parts coupled to the inner surface of the flexible hollow portion; and
    the plurality of movable parts configured to contact a material and including a control mechanism configured to induce controllable motion of the plurality of movable parts to generate a force for moving the material within the hollow portion.

2. The device of claim 1, wherein the flexible hollow portion comprises:
    a substantially tubular or cylindrical structure.

3. The device of claim 2, wherein the a substantially tubular or cylindrical structure comprises:
    at least one of a substantially expandable, or contractile structure.

4. The device of claim 2, wherein the substantially tubular or cylindrical structure flexible comprises:
    an expandable mesh.

5. The device of claim 2, wherein the substantially tubular or cylindrical structure comprises:
    a plurality of expandable segments coupled to the plurality of movable parts.

6. The device of claim 2, wherein the substantially tubular or cylindrical structure comprises:
    one or more of a metal, silicon, polymer, plastic, organic, or biodegradable material.

7. The device of claim 2, wherein the substantially tubular or cylindrical structure further comprises:
    a coating of one or more of a drug, a medicinal agent, a therapeutic agent, a biologically active agent, a chemical, a chemical compound, a surfactant, a steroid, a luminal-dilating agent, a luminal-contracting agent, an antibiotic or antifungal or antiviral agent, a protein, a nucleic acid or a polymer comprised of one or more nucleic acids, a macromolecule, a peptide, polymer, or a biodegradable material.

8. The device of claim 1, wherein the flexible hollow portion comprises:
    a shape or configuration for placement in the location.

9. The device of claim 1, wherein the flexible hollow portion comprises:
    one or more forks or branches.

10. The device of claim 1, wherein the flexible hollow portion comprises:
    a substantially smooth inner surface.

11. The device of claim 1, wherein the flexible hollow portion comprises:
    an inner surface with a low coefficient of friction operable for low-impedance flow of air or fluid.

12. The device of claim 1, wherein the flexible hollow portion comprises:
    an outer surface with a surface modification operable for adhesion, adherence or positioning to the location in the host.

13. The device of claim 12, wherein the surface modification comprises:
    one or more of a groove, bump, ridge, ring or contour.

14. The device of claim 1, wherein the host includes:
    an animal or a plant.

15. The device of claim 1, wherein the plurality of movable parts comprises:
one or more of a gel, a hydrogel, a colloid, a polymer, an oscillating polymer, an electro-active polymer, a polymer, an electro- or magneto-strictive material, a linear motor-device, or a material coated with a biologically compatible material.

16. The device of claim 1, wherein the plurality of movable parts comprises:
a low-level gait or motion for moving fluid, particles, fluidized particles, mucus, exudate or debris.

17. The device of claim 1, wherein the plurality of movable parts comprises:
a high-level gait or motion for moving fluid, particles, fluidized particles, mucus, exudate, or debris.

18. The device of claim 1, wherein the control mechanism comprises:
an actuator, a motor, a biomolecular motor, or a device operable for providing motion coupled to the plurality of movable parts.

19. The device of claim 1, wherein the control mechanism comprises:
a MEMS device.

20. The device of claim 1, wherein the control mechanism comprises:
a magnetic material.

21. The device of claim 1, wherein the control mechanism comprises:
an electroactive polymer.

22. The device of claim 1, wherein the control mechanism comprises:
an electrorestrictive material.

23. The device of claim 1, wherein the device further comprises:
a mechanism for dispensing of at least one of a drug, a medicinal agent, a therapeutic agent, a biologically active agent, a chemical, a chemical compound, a surfactant, a steroid, a luminal-dilating agent, a luminal-contracting agent, an antibiotic or antifungal or antiviral agent, a protein, a nucleic acid or a polymer comprised of one or more nucleic acids, a macromolecule, a peptide, a polymer, or a biodegradable material.

24. A device, comprising:
a flexible hollow portion with an outer surface and an inner surface;
a plurality of movable parts coupled to the inner surface of the flexible hollow portion, the plurality of movable parts configured to contact a material and configured to generate a movable force on the material; and
a controller configured to provide an electric, magnetic, acoustic, optical or electromagnetic field to the plurality of movable parts for controlling the plurality of movable parts or the flexible hollow portion.

25. A system, comprising:
a device including a flexible hollow portion with an outer surface and an inner surface and wherein the flexible hollow portion is sized for placement in a location in a host;
a plurality of movable parts coupled to the inner surface of the flexible hollow portion, the plurality of movable parts operable as a group and configured for contacting and moving particles; and
an external or internal a controller configured to provide an electric, magnetic, acoustic, optical or electromagnetic field for controlling the device.

26. A device, comprising:
a flexible hollow portion with an outer surface and an inner surface;
a plurality of movable parts coupled to the inner surface of the flexible hollow portion, the plurality of movable parts configured to contact a material and including a control mechanism configured to induce controllable motion of the plurality of movable parts to generate a force for moving the material within the hollow portion; and
a reservoir for storing one or more of a drug, a medicinal agent, a therapeutic agent, a biologically active agent, a chemical, a chemical compound, a surfactant, a steroid, a luminal-dilating agent, a luminal-contracting agent, an antibiotic or antifungal or antiviral agent, a protein, a nucleic acid or a polymer comprised of one or more nucleic acids, a macromolecule, a peptide, a polymer, or a biodegradable material.

27. The device of claim 26, wherein the flexible hollow portion further comprises:
one or more movable parts coupled to the outer surface of the flexible hollow portion.

28. The device of claim 26, wherein the device further comprises:
a mechanism for powering the device.

29. The device of claim 28, wherein the mechanism for powering the device further comprises:
a mechanism for obtaining or storing energy.

30. A method of making a device, comprising:
forming a supporting passage implantable in a host;
coupling a plurality of moving parts to the supporting passage, wherein the plurality of moving parts are configured to contact a material and include a control mechanism configured to induce controllable motion of the plurality of movable parts to generate a force for moving the material within the hollow portion; and
sizing the supporting passage and the plurality of moving parts coupled to the supporting passage for placement in a location in the host.

31. The method of claim 30, wherein the method further comprises:
forming the supporting passage wherein at least a portion of the supporting passage is at least one of substantially flexible, compressible, or expansile.

32. The method of claim 30, wherein the method further comprises:
forming the supporting passage including a substantially expandable tubular or cylindrical part coupled to the plurality of moving parts.

33. The method of claim 30, wherein the method further comprises:
forming the supporting passage including an expandable mesh coupled to the plurality of moving parts.

34. The method of claim 30, wherein the method further comprises:
forming the supporting passage coupled to the plurality of moving parts configured for placement in the location in the host.

35. The method of claim 30, wherein the method further comprises:
forming a bifurcated supporting passage.

36. The method of claim 30, wherein the method further comprises:
forming the supporting passage or plurality of moving parts with one or more of a metal, silicon, polymer, plastic, inorganic, organic, or biodegradable material.

37. The method of claim 30, wherein the method further comprises:
coating at least a portion of the supporting passage or plurality of moving parts with a biocompatible material, polymer, biodegradable material, drug, medicinal agent, or therapeutic agent.

38. The method of claim 30, wherein the method further comprises:
producing a smooth surface in at least a portion of the interior of the supporting passage.

39. The method of claim 30, wherein the method further comprises:
making surface modifications in the exterior of the supporting passage operable for attaching to or positioning about the location in the host.

40. The method of claim 39, wherein the method further comprises:
forming surface modifications including grooves, contours, ridges, rings or bumps in the exterior of the supporting passage.

41. The method of claim 30, wherein the method further comprises:
forming the supporting passage or the plurality of moving parts including one or more of a gel, a hydrogel, a colloid, a polymer, an oscillating polymer, an electro-active polymer, a polymer, or a material coated with a biologically-compatible material.

42. The method of claim 30, wherein the method further comprises:
orienting the plurality of moving parts radially outward.

43. The method of claim 30, wherein the method further comprises:
configuring the plurality of moving parts to define a low-level gait or motion.

44. The method of claim 30, wherein the method further comprises:
configuring the plurality of moving parts to define a high-level gait or motion.

45. The method of claim 30, wherein the method further comprises:
operably-coupling an actuator, a motor, a biomolecular motor, or a device operable for providing motion to the plurality of moving parts.

46. The method of claim 30, wherein the method comprises:
forming the supporting passage with a custom size, shape, configuration, or dimension for placing in a trachea, a bronchi, a bronchial tree, a urogenital tract, a gastrointestinal tract, a pulmonary tract, a neurovascular system, or a vascular system.

47. The method of claim 30, wherein the method comprises:
forming the supporting passage with a custom size, shape, configuration, or dimension for replacing or functionally supplanting at least a portion of a trachea, a bronchi, a bronchial tree, a urogenital tract, a gastrointestinal tract, a pulmonary tract, a neurovascular system, or a vascular system.

48. The method of claim 30, wherein the method further comprises:
coupling an external control system to the plurality of moving parts or the supporting passage.

49. The method of claim 30, wherein the method further comprises:
including an external control system for remotely operating or manipulating the device.

50. The method of claim 30, wherein the method further comprises:
coupling a monitor to the supporting passage.

51. The method of claim 30, wherein the method further comprises:
coupling a debris-removing, debris-displacing or debris-relocating system to the supporting passage.

52. The method of claim 30, wherein the method further comprises:
providing a storage system for storing at least one of a drug, a medicinal agent, a therapeutic agent, a biologically active agent, a chemical, a chemical compound, a surfactant, a steroid, a luminal-dilating agent, a luminal-contracting agent, an antibiotic or antifungal or antiviral agent, a protein, a nucleic acid or a polymer comprised of one or more nucleic acids, a macromolecule, a peptide, a polymer, or a biodegradable material.

53. The method of claim 30, wherein the method further comprises:
coating at least a portion of the device with at least one of a drug, a medicinal agent, a therapeutic agent, a biologically active agent, a chemical, a chemical compound, a surfactant, a steroid, a luminal-dilating agent, a luminal-contracting agent, an antibiotic or antifungal or antiviral agent, a protein, a nucleic acid or a polymer comprised of one or more nucleic acids, a macromolecule, a peptide, a polymer, or a biodegradable material.

54. The method of claim 30, wherein the method further comprises:
including a mechanism for releasing one or more of a drug, a medicinal agent, a therapeutic agent, a biologically active agent, a chemical, a chemical compound, a surfactant, a steroid, a luminal-dilating a luminal-contracting agent, an antibiotic or antifungal or antiviral agent, a protein, a nucleic acid or a polymer comprised of one or more nucleic acids, a macromolecule, a peptide, a polymer, or a biodegradable material.

55. The method of claim 30, wherein the method further comprises:
storing energy internal or external to the device.

56. The method of claim 30, wherein the method further comprises:
providing a mechanism for obtaining power.

57. The method of claim 30, wherein the method further comprises:
coupling the plurality of moving parts to at least one of an interior wall or an exterior wall of the supporting passage.

58. A method of making a device, comprising:
forming a supporting passage implantable in a host;
coupling a plurality of moving parts to the supporting passage, the the plurality of movable parts configured to contact a material and including a control mechanism configured to induce controllable motion of the plurality of movable parts to generate a force for moving the material within the hollow portion;
sizing the supporting passage and the plurality of moving parts coupled to the supporting passage for placement in a location in the host; and
including an actuator operable for controlling the motion or direction of the one or more moving parts.

59. A method, comprising:
placing a hollow expandable device in a luminal portion of a recipient wherein the hollow expandable device includes an outer surface and an inner surface, wherein a plurality of moving parts are coupled to the inner surface, wherein the plurality of movable parts including a control mechanism configured to induce controllable motion of the plurality of movable parts to generate a force for moving material within the hollow portion;

positioning the hollow expandable device in the lumen of an organ; and monitoring the hollow expandable device.

60. The method of claim 59, wherein the method further comprises:

adjusting, guiding, positioning, directing, or activating the hollow expandable device.

61. The method of claim 59, wherein the method further comprises:

removing the hollow expandable device.

62. The method of claim 59, wherein the method further comprises:

activating the one or more moving parts coupled to the hollow expandable device to move fluid, particles, fluidized particles, mucus, exudate or debris.

63. The method of claim 59, wherein the method further comprises:

placing the hollow expandable device in a trachea, a bronchi, a bronchial tree, a urogenital tract, a gastrointestinal tract, a pulmonary tract, a neurovascular system, or a vascular system.

64. The method of claim 59, wherein the method further comprises:

controlling a motion or directionality of the one or more of moving parts.

65. The method of claim 59, wherein the method further comprises:

adjusting the orientation of the one or more of moving parts.

66. The method of claim 59, wherein the method further comprises:

placing the hollow expandable device wherein the hollow expandable device has at least one fork.

67. The method of claim 66, wherein the method further comprises:

positioning the at least one fork.

68. The method of claim 59, wherein the method further comprises:

removing any debris.

69. The method of claim 59, wherein the method further comprises:

monitoring the hollow expandable device remotely.

70. The method of claim 59, wherein the method further comprises:

positioning the hollow expandable device and the one or more of moving parts remotely.

71. The method of claim 59, wherein the method further comprises:

charging the hollow expandable device.

72. The method of claim 59, wherein the method further comprises:

delivering a drug, a medicinal agent, a therapeutic agent, a biologically active agent, a chemical, a chemical compound, a surfactant, a steroid, a luminal-dilating agent, a luminal-contracting agent, an antibiotic or antifungal or antiviral agent, a protein, a nucleic acid or a polymer comprised of one or more nucleic acids, a macromolecule, a peptide, polymer, or a biodegradable material.

73. A method, comprising:

placing a hollow expandable device in a luminal portion of a host wherein the interior of the hollow expandable device is coupled to one or more moving parts, the one or more moving parts configured for contacting and moving particles;

positioning the hollow expandable device in the lumen of an organ;

monitoring the hollow expandable device; and applying at least one of an external electric, magnetic, acoustic, optical or electromagnetic field for removing fluid, particles, fluidized particles, mucus, exudate or debris.

74. A method, comprising:

placing a hollow flexible device in a luminal portion of a host, the hollow flexible device having an interior configured to permit entry and exit of a material;

wherein the interior of the hollow flexible device includes one or more moving parts, the one or more moving parts configured to contact the material and to controllably move the material;

positioning the hollow flexible device in the lumen of an organ; and applying at least one of an external electric, magnetic, acoustic, optical or electromagnetic field to the one or more movable parts.

* * * * *

UNITED STATES PATENT AND TRADEMARK OFFICE
CERTIFICATE OF CORRECTION

| | | |
|---|---|---|
| PATENT NO. | : 8,092,549 B2 | Page 1 of 1 |
| APPLICATION NO. | : 10/949186 | |
| DATED | : January 10, 2012 | |
| INVENTOR(S) | : W. Daniel Hillis et al. | |

It is certified that error appears in the above-identified patent and that said Letters Patent is hereby corrected as shown below:

IN THE CLAIMS:

Column 16, line 52, claim 58, the line reading "--passage, the the plurality of movable parts configured to--" should read --passage, the plurality of movable parts configured to--

Signed and Sealed this
Sixth Day of March, 2012

David J. Kappos
*Director of the United States Patent and Trademark Office*